(12) United States Patent
Oikawa et al.

(10) Patent No.: US 6,653,507 B2
(45) Date of Patent: Nov. 25, 2003

(54) PROCESS FOR PRODUCING OPTICALLY ACTIVE 3,3,3-TRIFLUORO-2-HYDROXY-2-METHYLPROPIONIC ACID, AND SALT THEREOF

(75) Inventors: Miyuki Oikawa, Ibaraki (JP); Hideki Ushio, Takatsuki (JP); Isao Kurimoto, Suita (JP); Takayuki Higashii, Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/147,966

(22) Filed: May 20, 2002

(65) Prior Publication Data

US 2002/0143212 A1 Oct. 3, 2002

Related U.S. Application Data

(62) Division of application No. 09/632,804, filed on Aug. 4, 2000, now Pat. No. 6,403,832.

(30) Foreign Application Priority Data

Aug. 4, 1999 (JP) ............................................ 11-221065
Nov. 25, 1999 (JP) ............................................ 11-333924

(51) Int. Cl.$^7$ ...................... C07C 211/00; C07C 209/00
(52) U.S. Cl. ........................ 564/305; 564/415; 564/463; 564/489
(58) Field of Search ................................ 564/305, 415, 564/463, 489

(56) References Cited

U.S. PATENT DOCUMENTS 5,726,325 A  3/1998  Yoshida et al.
6,211,244 B1 * 4/2001  Van Wagenen et al. ...... 514/649

FOREIGN PATENT DOCUMENTS

WO     A19714672    4/1997
WO     WO 9738124   10/1997

OTHER PUBLICATIONS

R.A. Darrall et al. Journal of Chemical Society "Organic Fluorides. Part IX" 1951, pp. 2329–2332.
Cyrus J. Ohnmacht, et al.Journal of Medicinal Chemistry, 1996, vol. 39, No. 23 pp. 4592–4601.

* cited by examiner

Primary Examiner—Alan L. Rotman
Assistant Examiner—Hector M Reyes
(74) Attorney, Agent, or Firm—Birch, Stewart, Kolasch & Birch, LLP

(57) ABSTRACT

There are disclosed are A diastereomer salt of formula (1):

$$CH_3-\underset{\underset{OH}{|}}{\overset{\overset{CF_3}{|}}{C^*}}-COO^-H_2^+N-\underset{\underset{H}{|}}{\overset{\overset{R_3\ R_2}{|\ \ |}}{C^*}}-R_1, \quad (1)$$

a process for producing the same, a process for producing optically active 3,3,3-trifluoro-2-hydroxy-2-methylpropionic acid of formula (2'):

$$CH_3-\underset{\underset{OH}{|}}{\overset{\overset{CF_3}{|}}{C^*}}-COOH \quad (2')$$

a novel optically active amine compound of formula (4):

$$R_{11}-\underset{\underset{H}{|}}{\overset{\overset{R_{21}}{|}}{C^*}}-NH-CH_2-R_{31} \quad (4)$$

a novel optically active amine compound of formula (8):

<chemical structure (8): pentasubstituted phenyl (X1–X5) with C*(R22)(H)–NH–CH2–R32> an imine compound of formula (7) or (11):

$$R_{11}-\underset{\underset{H}{|}}{\overset{\overset{R_{21}}{|}}{C^*}}-N=CH-R_{31} \quad (7)$$

<chemical structure (11): pentasubstituted phenyl (X1–X5) with C*(R22)(H)–NH=CH–R32>

10 Claims, No Drawings

PROCESS FOR PRODUCING OPTICALLY ACTIVE 3,3,3-TRIFLUORO-2-HYDROXY-2-METHYLPROPIONIC ACID, AND SALT THEREOF

This application is a divisional of application Ser. No. 09/632,804, filed on Aug. 4, 2000, now U.S. Pat. No. 6,403,832 the entire contents of which are hereby incorporated by reference and for which priority is claimed under 35 U.S.C. §120; and this application claims priority of Application Ser. No. H11-221065 & H11-333924 filed in JAPAN on Aug. 4, 1999 and Nov. 25, 1999 under 35 U.S.C. §119.

BACKGROUND OF THE INVENTION

1. Field of the Invention

The present invention relates to a method for producing optically active 3,3,3-trifluoro-2-hydroxy-2-methylpropionic acid by resolving racemic 3,3,3-trifluoro-2-hydroxy-2-methylpropionic acid with an optically active amine compound, novel optically active amine compound therefor and its production process.

2. Description of Related Art

Optically active 3,3,3-trifluoro-2-hydroxy-2-methylpropionic acid is a useful intermediate compound of pharmaceuticals for urinary incontinence as described in WO97/14672 and also of agrochemicals.

There have been reported a method in which racemic 3,3,3-trifluoro-2-hydroxy-2-methylpropionic acid is resolved with optically active α-methylbenzylamine (J. Med. Chem., 1996, 39, 4592–4601) and a method in which racemic 3,3,3-trifluoro-2-hydroxy-2-methylpropionic acid is optically resolved with brucine and followed by repeated recrystallizations (J. Chem. Soc., 1951, 2329–2332).

SUMMARY OF THE INVENTION

An object of the present invention is to provide a diastereomer salt comprising a specific optically active amine and optically active 3,3,3-trifluoro-2-hydroxy-2-methylpropionic acid which is suitable for producing optically active 3,3,3-trifluoro-2-hydroxy-2-methylpropionic acid having good optical purity.

another object of the invention is to provide a process for producing optically active 3,3,3-trifluoro-2-hydroxy-2-methylpropionic acid in industrially advantageous manner.

further objects of the invention are to provide novel optically active amine compounds suitable for optical resolution, intermediate compounds for producing the optically active amines, and processes for producing the intermediate compounds.

The present invention provides:

1. A diastereomer salt of formula (1):

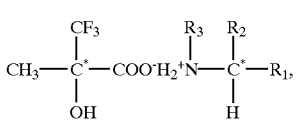

(1)

wherein each asymmetric carbon atom denoted by the symbol * is independently in S configuration or R configuration.

$R_1$ represents a lower alkyl group which may be substituted with a hydroxy group, or an optionally substituted aryl group, $R_2$ represents a lower alkyl group which may be substituted with a hydroxy group, or an optionally substituted aralkyl group, and $R_3$ represents a lower alkyl group which may be substituted with a hydroxy group, a hydrogen atom, a cyclohexyl group, or an optionally substituted aralkyl group, provided that $R_1$ and $R_2$ are not the same, and when $R_1$ is a phenyl group and $R_2$ is a methyl group, $R_3$ is not a hydrogen atom;

2. A method for producing a diastereomer salt of formula (1) as defined above, which comprises contacting racemic 3,3,3-trifluoro-2-hydroxy-2-methylpropionic acid of formula (2):

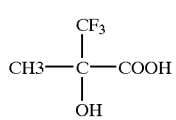

(2)

with an optically active amine of formula (3):

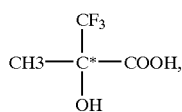

(3)

wherein the symbol *, $R_1$, $R_2$, and $R_3$ respectively represent the same as defined above to form diastereomer salt(s), and separating said diastereomer salt of formula (1):

3. A method for producing an optically active 3,3,3-trifluoro-2-hydroxy-2-methylpropionic acid of formula (2'):

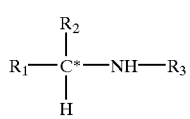

(2')

wherein an asymmetric carbon atom denoted by the symbol * is in S configuration or R configuration, which comprises treating the salt of formula (1) as defined above, with an acid, or a base and an acid;

4. An optically active amine compound of formula (4):

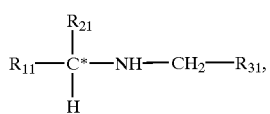

(4)

wherein an asymmetric carbon atom denoted by the symbol * is in S configuration or R configuration, $R_{11}$ represents an aryl group which may be substituted with at least one group selected from a C1–C4 alkyl group, a C1–C4 alkoxy group, a nitro group and a halogen atom, $R_{21}$ represents a C1–C4 alkyl group, or an aralkyl group which may be substituted, and $R_{31}$ is a 3-benzyloxyphenyl group of a 4-benzyloxyphenyl group, or a salt thereof;

5. A method for producing an optically active amine compound of formula (4) as defined above, or a salt thereof, which comprises:
reducing an imine compound of formula (7);

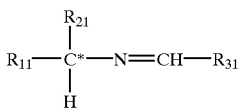
(7)

wherein the symbol *, $R_{11}$, $R_{21}$ and $R_{31}$ respectively have the same meaning as defined above, to a reduction reaction;

6. An imine compound of formula (7) as defined above,
7. A method for producing an imine compound of formula (7) as defined above, which comprises:
reacting an optically active amine of formula (5):

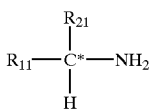
(5)

wherein the symbol * denotes an asymmetric carbon atom, $R_{11}$ and $R_{21}$ respectively represent the same as defined above, with a benzyloxybenzaldehyde of formula (6):

$R_{31}$—CHO (6)

wherein $R_{31}$ represents a 3-benzyloxyphenyl group or a 4-benzyloxyphenyl group;

8. An optically active amine compound of formula (8):

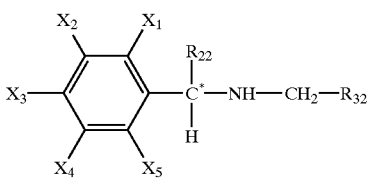
(8)

wherein $X_1$ represents a halogen atom, or a lower alkyl group,
$X_2$ to $X_5$ are the same or different and independently represent a hydrogen atom, a halogen atom, a nitro group or a lower alkyl group,
$R_{22}$ represents a lower alkyl group, and
$R_{32}$ represents an aryl group substituted with at least one group selected from a lower alkyl group, a lower alkoxy group, an aryl group, and an aryloxy group;

9. A method for producing an optically active amine compound of formula (8) as defined above, which comprises:
subjecting an imine compound of formula (11):

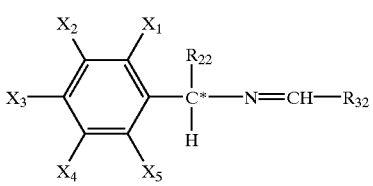
(11)

wherein $X_1$ and $X_5$, $R_{22}$ and $R_{32}$ are the same as defined above, to a reduction reaction.

10. An imine compound of formula (11) as defined above; and

11. A method for producing an imine compound of formula (11) as defined above, which comprises:
reacting an optically active amine compound of formula (9):

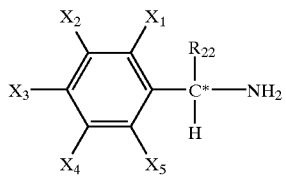
(9)

wherein $X_1$ to $X_5$ and $R_{22}$ are the same as defined above, with an aldehyde of formula (10):

$R_{32}$—CHO (10)

wherein $R_{32}$ represents the same as defined above.

DETAILED DESCRIPTION OF THE INVENTION

First a description will be made to the diastereomer salt of formula (1).

Racemic 3,3,3-trifluoro-2-hydroxy-2-methylpropionic acid (2) can be prepared by a known method as disclosed in J. Chem. Soc., 1951, 2329–2332 or the like.

The substituting groups $R_1$, $R_2$, and $R_3$ of the optically active amine compound of formula (3) will be explained below.

Examples of the lower alkyl group which may be substituted with a hydroxy group, in $R_1$, $R_2$, and $R_3$ include a C1–C4 alkyl group which may be substituted with a hydroxy group.

Specific examples thereof include a methyl group, an ethyl group, a n-propyl group, an isopropyl group, a t-butyl group, a sec-butyl group, an i-butyl group, a hydroxymethyl group, a 2-hydroyxethyl group, a 2-hydroxypropyl group, a 2-hydroxy-2-methylpropyl group and the like.

In $R_3$, the hydroxy group which may be present on the alkyl moiety of the alkyl group which may be substituted with a hydroxy group is not on a carbon atom which is bound with the nitrogen atom.

Examples of the optionally substituted aryl group, in $R_1$ include a phenyl group, a naphthyl group and the like, all of which may be substituted with at least one group selected from a C1–C4 alkyl group, a C1–C4 alkoxy group, a nitro group and a halogen atom.

The C1–C4 alkyl group on the aromatic ring of the aryl groups includes a methyl group, an ethyl group, a n-propyl group, an isopropyl group, a t-butyl group, a sec-butyl group and an i-butyl group.

The C1–C4 alkoxy group on the aromatic ring of the aryl groups includes a methoxy group, an ethoxy group, a n-proproxy group, an isopropoxy group, a t-butoxy group and the like.

Examples of the halogen atom on the aromatic ring include a fluorine atom, a chlorine atom, a bromine atom and an iodine atom.

Specific examples of the optionally substituted aryl group include a phenyl group, a naphthyl group, a 4-methylphenyl group, a 4-ethylphenyl group, a 4-propylphenyl group, a 4-isopropylphenyl group, a 4-t-butylphenyl group, a 2,5-dimethylphenyl group, a 2,4,6-trimethylphenyl group, a 2-fluorophenyl group, a 3-fluorophenyl group, a 4-fluorophenyl group, a 2-chlorophenyl group, a 3-chlorophenyl group, a 4-chlorophenyl group, a 2,4-dichlorophenyl group, a 2,3-dichlorophenyl group, a 4-bromophenyl group, a 2-methoxyphenyl group, a 4-methoxyphenyl group, a 2-ethoxyphenyl group, a 2-proproxyphenyl group, a 3,4-dimethoxyphenyl group, a 2-methoxy-5-fluorophenyl group and the like.

The optionally substituted aralkyl group, in $R_2$ and $R_3$ include a C7–C12 aralkyl group
- of which aryl group may be substituted with at least one group selected from a C1–C4 alkyl group, a C1–C4 alkoxy group, a nitro group, a halogen atom, a C6–C10 aryl group, a C6–C10 aryloxy group, a C7–C12 aralkyl group and a C7–C12 aralkyloxy group, the last four of which may be substituted on each aromatic ring with at least one group selected from a C1–C4 alkyl group, a C1–C4 alkoxy group and a halogen atom, and
- of which alkyl group (e.g., a methyl or ethyl group) may be substituted with a hydroxy pump.

The aryl groups in the above-described aryl, arloxy, aralkyl and aralkyloxy groups include a C6–C10 aryl group such as a phenyl or naphthyl group.

The alkyl moiety, in the aralkyl group, which may be substituted with a hydroxyl group include a methyl group or ethyl group, a hydroxymethyl group or hydroxyethyl group.

The C1–C4 alkyl group, the C1–C4 alkoxy group and the halogen atom, all of which may be present on the aryl group include the same groups as specified above.

Specific examples of the aryloxy group include a phenoxy, 1-naphthoxy and 2-naphthoxy group and the like.

Specific examples of the aralkyl group include a benzyl group, a phenylethyl group, 1-naphthylmethyl group, 2-naphthylmethyl group and the like.

Specific examples of the aralkyloxy group include a benzyloxy group, 1-naphthylmethoxy group, 2-naphthylmethoxy group and the like.

Specific examples of the optionally substituted aralkyl group, in $R_2$ and $R_3$ include a benzyl group, a naphthylmethyl group, a 3-methylbenzyl group, a 4-methylbenzyl group, a 4-ethylbenzyl group, a 4-propylbenzyl group, a 4-isopropylbenzyl group, a 4-t-butylbenzyl group, a 2,5-dimethylbenzyl group, a 2,4,6-trimethylbenzyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2,4-dichlorobenzyl group, a 2,3-dichlorobenzyl group, a 4-bromobenzyl group, a 2-methoxybenzyl group, a 3-methoxybenzyl group, a 4-methoxybenzyl group, a 2-ethoxybenzyl group, a 2-propoxybenzyl group, a 3,4-dimethoxybenzyl group, a 2-methoxy-5-fluorobenzyl group, a 2-phenylethyl group, a α-hydroxybenzyl group, an α-hydroxy-4-methylbenzyl group, an α-hydroxy-4-methoxybenzyl group, an α-hydroxy-4-nitrobenzyl group, an α-hydroxy-4-chlorobenzyl group, a 3-phenoxybenzyl group, a 4-phenoxybenzyl group, a 3-phenylbenzyl group, a 4-phenylbenzyl group, a 3-benzyloxybenzyl group, a 4-benzyloxybenzyl group and the like.

Specific examples of the optically active amine (3) include optically active isomers of α-ethylbenzylamine, α-propylbenzylamine, α-isopropybenzylamine, α,4-dimethylbenzylamine, α2,5-trimethylbenzylamine, α,2,4,6-tetramethylbenzylamine, α-methyl-4-isopropylbenzylamine, 2-fluoro-α-methylbenzylamine, 3-fluoro-α-methylbenzylamine, 4-fluoro-α-methylbenzylamine, 4-bromo-α-methylbenzylamine, 2-chloro-α-methylbenzylamine, 3-chloro-α-methylbenzylamine, 4-chloro-α-methylbenzylamine, 2,3-dichloro-α-methylbenzylamine, 2,4-dichloro-α-methylbenzylamine, 2-methoxy-α-methylbenzylamine, 4-methoxy-α-methylbenzylamine, 2-ethoxy-α-methylbenzylamine, 3,4-dimethoxy-α-methylbenzylamine, 5-fluoro-2-methoxy-α-methylbenzylamine, α,β-diphenylethylamine, 1-phenyl-2-(p-tolyl)ethylamine, α-phenyl-β-(3-methoxyphenyl)ethylamine, α-phenyl-β-(4-chlorophenyl)ethylamine, α,γ-diphenylpropylamine, α-methyl-1-naphthylamine, α-methyl-2-naphthylmethylamine, N-benzyl-α-methylbenzylamine, N-(2-naphthylmethyl)-α-methylbenzylamine, N-(3-benzyloxybenzyl)-α-methylbenzylamine, N-(4-phenylbenzyl)-α-methylbenzylamine, N-(3-benzyloxybenzyl)-1-phenyl-2-(p-tolyl)ethylamine, N-(4-phenylbenzyl)-1-phenyl-2-(p-tolyl)ethylamine, N-benzyl-2,4-dichloro-α-methylbenzylamine, N-(3-benzyloxybenzyl)-2,4-dichloro-α-methylbenzylamine, N-(4-phenylbenzyl)-2,4-dichloro-α-methylbenzylamine, N-(3-chlorobenzyl)-α-methylbenzylamine, N-(4-chlorobenzyl)-α-methylbenzylamine, N-(3-nitrobenzyl)-α-methylbenzylamine, N-(4-nitrobenzyl)-α-methylbenzylamine, norephedrine, 2-amino-1-phenyl-1-butanol, 2-amino-3-methyl-1-phenyl-1-butanol, 2-amino-1-(4-methylphenyl)-1-propanol, 2-amino-1-(4-nitrophenyl)-1-propanol, 2-amino-1-(4-chlorophenyl)-1-propanol, 2-amino-1,2-diphenylethanol, 2-amino-1-phenyl-2-(p-tolyl)ethanol, 2-amino-1-phenyl-2-(4-chlorophenyl)ethanol, 2-amino-1-phenyl-2-(4-methoxyphenyl)ethanol, N-benzyl-2-amino-1-phenyl-1-propanol, N-benzyl-2-amino-1-phenyl-1butanol, N-benzyl-2-amino-3methyl-1-phenyl-1butanol, N-benzyl-2-amino-1-(4-methylphenyl)-1-propanol, N-benzyl-2-amino-1-(4-nitrophenyl)-1-propanol, N-benzyl-2-amino-1-(4-chlorophenyl)-1-propanol, N-benzyl-2-amino-1,2-diphenylethanol, N-benzyl-2-amino-1-phenyl-2-(p-tolyl)ethanol, N-benzyl-2-amino-1-phenyl-2-(4-chlorophenyl)ethanol, N-benzyl-2-amino-1-phenyl-2-(4-methoxyphenyl)ethanol, N-(3-benzyloxybenzyl)-2-amino-1-phenyl-1propanol, N-(4-phenylbenzyl)-2-amino-1-phenyl-1-propanol, N-(2-naphthylmethyl)-2-amino-1-phenyl-1-propanol, N-(4-methylbenzyl)-2-amino-1-phenyl-1-propanol, N-(3-chlorobenzyl)-2-amino-1-phenyl-1-propanol, N-(4-nitrobenzyl)-2-amino-1-phenyl-1-propanol, N-(4-methoxybenzyl)-2-amino-1-phenyl-1-propanol, N-(2,5-dimethoxybenzyl)-2-amino-1-phenyl-1-propanol, N-(3-methoxybenzyl)-2-amino-1-phenyl-1-propanol, and the like.

Among these optically active amines (3), preferred are optical isomers of a α-4-dimethylbenzylamine, N-benzyl-α-methylbenzylamine, N-(3-benzyloxybenzyl)-α-methylbenzylamine, N-(4-phenylbenzyl)-α-methylbenzylamine, N-(2-naphthylmethyl)-α-methylbenzylamine, N-(3-chlorobenzyl)-α-methylbenzylamine, 1-phenyl-2-(p-tolyl)ethylamine, N-benzyl-1-phenyl-2-(p-tolyl)ethylamine, N-benzyl-2,4-dichloro-α-methylbenzylamine, N-(3-benzyloxybenzyl)-2,4-dichloro-α-methylbenzylamine, N-(4-phenylbenzyl)-2,4-dichloro-α-methylbenzylamine, norephedrine and the like.

More preferred are
- an optically active amine compound of formula (3), wherein $R_1$ is a phenyl group, $R_2$ is a 4-methylbenzyl group and $R_3$ is a benzyl group,
- an optically active amine compound of formula (3), wherein $R_1$ is a methyl group, $R_2$ is a α-hydroxybenzyl group and $R_5$ is a hydrogen atom,
- an optically active amine compound of formula (3), wherein $R_1$ is a 2,4-dichlorophenyl group, $R_2$ is a methyl group and $R_3$ is a 3-benzyloxybenzyl group, an optically active amine compound of formula (3), wherein $R_1$ is a 2,4-dichlorophenyl group, $R_2$ is a methyl group and $R_3$ is a 4-phenylbenzyl group, which are N-benzyl-1-phenyl-2-(p-tolyl)ethylamine, N-(3-benzyloxybenzyl)2,4-dichloro-α-methylbenzylamine, N-(4-phenylbenzyl)-2,4-dichloro-α-methylbenzylamine, and norephedrine.

The diastereomer salt of formula (1) as defined above can be produced by a process which comprises contacting racemic, 3,3,3-trifluoro-2-hydroxy-2-methylpropionic acid formula (2) with an optically active amine of formula (3), typically in a solvent, to obtain diastereomer salt(s), and isolating the desired diastereomer salt of formula (1).

The amount of the optically active amine (3) to be used is usually approximately from 0.2 to 3moles, preferably approximately from 0.4 to 1.5 moles per mole of racemic 3,3,3-trifluoro-2-hydroxy-2-methylpropionic acid (2).

The diastereomer salt of formula (1) formed in the resulting reaction mixture is usually precipitated, wherein the reaction mixture is usually in solution form and optionally a solvent may be used for dissolving said reaction mixture.

Precipitation of the desired salt may be accomplished on standing, stirring, inoculating of seed crystals, cooling and/or concentrating said solution, and precipitated salts are usually isolated, for example, by filtration or the like, and optionally followed by washing and/or drying.

Contacting the 3,3,3-trifluoro-2-hydroxy-2-methylpropionic acid (2) with the optically active amine (3), standing, stirring, cooling and/or concentrating of the solution of the diastereomer salts are usually conducted within a temperature range of from a melting point of the solution to the boiling point of the solvent, if employed, or typically between from 31 20 to 60° C.

Examples of the solvent to be used include alcohols such as methanol, ethanol, isopropyl alcohol or the like, ketones such as acetone, methyl ethyl ketone, methyl isobutyl ketone or the like, ethers such as diethyl ether, t-butyl methyl ether, n-butyl ether, tetrahydrofuran or the like, esters such as ethyl acetate, aliphatic hydrocarbons such as n-hexane, n-heptane, cyclohexane or the like, aromatic hydrocarbons such as benzene, toluene, xylene or the like, halogenated hydrocarbons such as chloroform, dichloromethane, dichloroethane, chlorobenzene or the like, aprotic polar solvents such as dimethylformamide, acetonitrile or the like, and water, etc. The solvent may be used alone or as a mixture thereof.

The amount of the solvent to be used may be optionally set depending on the kind of the optically active amine (3), the kind of the solvent and the like, but is usually within the range of from 1to 50 parts by weight per 1 part by weight of 3,3,3-trifluoro-2-hydroxy-2-methylpropionic acid (2).

Examples of the diastereomer salt of formula (1) include salts comprising optically active 3,3,3-trifluoro-2-hydroxy-2-methylpropionic acid (2') having either S or R configuration with respect to the asymmetric carbon atom designated by *, and optically active amine of formula (3) as specified above having either S or R configuration with respect to the asymmetric carbon atom designated by *.

The optically active 3,3,3-trifluoro-2-hydroxy-2-methylpropionic acid (2') can be obtained by a method, which comprises treating the salt of formula (1) as defined above, with an acid, or a base and an acid.

Optically active 3,3,3-trifluoro-2-hydroxy-2-methylpropionic acid (2') can be obtained, for example, by contacting the diastereomer salt (1) with an aqueous acid solution, or an acid and water, extracting the resulting aqueous acid layer with a hydrophobic solvent, and then concentrating the extract.

Alternatively, the diastereomer salt (1) may be contacted with an aqueous basic solution. After extracting the resulting aqueous basic layer with a hydrophobic solvent, the separated aqueous layer is acidified with an acid, extracting the aqueous acid layer with a hydrophobic solvent and then concentrating the extract to yield the optically active 3,3,3-trifluoro-2-hydroxy-2-methylpropionic acid (2')

Specific examples of the acid to be used include an inorganic acid such as hydrofluoric acid, hydrochloric acid, hydrobromic acid, sulfuric acid or the like. Among these acids, hydrochloric acid and sulfuric acid are particularly preferred.

The amount of the acid to be used is usually approximately from 1to 200 moles, preferably approximately from 2to 20 moles per mol of the diastereomer salt (1).

Specific examples of the base to be used include alkali metal hydroxide such as lithium hydroxide, sodium hydroxide, potassium hydroxide or the like, alkaline earth metal hydroxides such as magnesium hydroxide, calcium hydroxide or the like, alkali carbonates such as sodium carbonate, potassium carbonate or the like, alkali hydrogencarbonates such as sodium hydrogencarbonate, potassium hydrogencarbonate or the like, etc.

The amount of the base to be used is usually approximately from 1to 200 moles, preferably approximately from 2 to 20 moles per mol of the diastereomer salt (1).

Specific examples of the hydrophobic solvent to be used for extraction in the present invention include ethers such as diethyl ether, t-butyl methyl ether, n-butyl ether, tetrahydrofuran or the like, esters such as ethyl acetate of the like, aliphatic hydrocarbons such as n-hexane, n-heptane, cyclohexane or the like, aromatic hydrocarbons such as benzene, toluene, xylene or the like, halogenated hydrocarbons such as chloroform, dichloromethane, dichloroethane, chlorobenzene or the like. The hydrophobic solvent may be used alone or as a mixture thereof.

The amount of the hydrophobic solvent to be used for extraction varies depending on the kind of the optically active amine (3) of the diastereomer salt, the kind of the solvent and the like, but it is usually within the range of from 1to 200 parts by weight per 1 part by weight of the diastereomer salt (1).

The amount of water, or aqueous acidic solution to be used for the dissolution of the diastereomeric salt (1) varies depending on the kind of the optically active amine (3) of the diastereomer salt and the like, but it is usually within the range of from 1to 200 parts by weight per 1 part by weight of the diastereomer salt (1).

The extraction is usually conducted at a temperature range of from the melting point to the boiling point of water and the solvent to be used, preferably approximately from 0 to 60° C.

According to the present invention, the optically active 3,3,3-trifluoro-2-hydroxy-2-methylpropionic acid which is useful as an intermediate for producing pharmaceuticals or agrochemicals, can be obtained in good optical purity in an industrial scale.

The optically active amine compound of formula (3) include novel optically active amine compounds of formulae (4) and (8).

In the novel optically active compound of formula (4), the aryl group which may be substituted with at least one group selected from a C1–C4 alkyl group, a C1–C4 alkoxy group, a nitro group and a halogen atom, in $R_{11}$ include the same groups as defined for $R_1$ above.

The optionally substituted aralkyl group and the C1–C4 alkyl group, in $R_{21}$ respectively represent the same groups as defined for $R_2$ above.

$R_{31}$ represents a 3-benzyloxyphenyl group or a 4-benzyloxyphenyl group.

Specific examples of the optically active amine compound (4) or a salt thereof include optically active isomers of N-(3-benzyloxybenzyl)-α-methylbenzylamine,
N-(3-benzyloxybenzyl)-α-ethylbenzylamine,
N-(3-benzyloxybenzyl)-α-propylbenzylamine,
N-(3-benzyloxybenzyl)-α-isopropylbenzylamine,
N-(3-benzyloxybenzyl)-α,4-dimethylbenzylamine,
N-(3-benzyloxybenzyl)-α,2,5-trimethylbenzylamine,
N-(3-benzyloxybenzyl)-α,2,4,6-tetramethylbenzylamine,
N-(3-benzyloxybenzyl)-α-methyl-4-isopropylbenzylamine,
N-(3-benzyloxybenzyl)-2-fluoro-α-methylbenzylamine,
N-(3-benzyloxybenzyl)-3-fluoro-α-methylbenzylamine,
N-(3-benzyloxybenzyl)-4-fluoro-α-methylbenzylamine,
N-(3-benzyloxybenzyl)-4-bromo-α-methylbenzylamine,
N-(3-benzyloxybenzyl)-2-chloro-α-methylbenzylamine,
N-(3-benzyloxybenzyl)-3-chloro-α-methylbenzylamine,
N-(3-benzyloxybenzyl)-4-chloro-α-methylbenzylamine,
N-(3-benzyloxybenzyl)-2,3-dichloro-α-methylbenzylamine,
N-(3-benzyloxybenzyl)-2,4-dichloro-α-methylbenzylamine,
N-(3-benzyloxybenzyl)-2-methoxy-α-methylbenzylamine,
N-(3-benzyloxybenzyl)-4-methoxy-α-methylbenzylamine,
N-(3-benzyloxybenzyl)-2-ethoxy-α-methylbenzylamine,
N-(3-benzyloxybenzyl)-3,4-dimethoxy-α-methylbenzylamine,
N-(3-benzyloxybenzyl)-5-fluoro-2-methoxy-α-methylbenzylamine,
N-(3-benzyloxybenzyl)-α,β-diphenylethylamine,
N-(3-benzyloxybenzyl)-1-phenyl-2-(p-tolyl)ethylamine,
N-(3-benzyloxybenzyl)-α-phenyl-β-(3-methoxyphenyl)ethylamine,
N-(3-benzyloxybenzyl)-α-phenyl-β-(4-chlorophenyl)ethylamine,
N-(3-benzyloxybenzyl)-α,γ-diphenylpropylamine,
N-(3-benzyloxybenzyl)-α-methyl-1-naphthylamine,
N-(3-benzyloxybenzyl)-α-methyl-2-naphthylmethylamine,
N-(4-benzyloxybenzyl)-α-methylbenzylamine,
N-(4-benzyloxybenzyl)-α-ethylbenzylamine,
N-(4-benzyloxybenzyl)-α-propylbenzylamine,
N-(4-benzyloxybenzyl)-α-isopropylbenzylamine,
N-(4-benzyloxybenzyl)-α,4-dimethylbenzylamine,
N-(4-benzyloxybenzyl)-α,2,5-trimethylbenzylamine,
N-(4-benzyloxybenzyl)-α,2,4,6-tetramethylbenzylamine,
N-(4-benzyloxybenzyl)-α-methyl-4-isopropylbenzylamine,
N-(4-benzyloxybenzyl)-2-fluoro-α-methylbenzylamine,
N-(4-benzyloxybenzyl)-3-fluoro-α-methylbenzylamine,
N-(4-benzyloxybenzyl)-4-fluoro-α-methylbenzylamine,
N-(4-benzyloxybenzyl)-4-bromo-α-methylbenzylamine,
N-(4-benzyloxybenzyl)-2-chloro-α-methylbenzylamine,
N-(4-benzyloxybenzyl)-3-chloro-α-methylbenzylamine,
N-(4-benzyloxybenzyl)-4-chloro-α-methylbenzylamine,
N-(4-benzyloxybenzyl)-2,3-dichloro-α-methylbenzylamine,
N-(4-benzyloxybenzyl)-2,4-dichloro-α-methylbenzylamine,
N-(4-benzyloxybenzyl)-2-methoxy-α-methylbenzylamine,
N-(4-benzyloxybenzyl)-4-methoxy-α-methylbenzylamine,
N-(4-benzyloxybenzyl)-2-ethoxy-α-methylbenzylamine,
N-(4-benzyloxybenzyl)-3,4-dimethoxy-α-methylbenzylamine,
N-(4-benzyloxybenzyl)-5-fluoro-2-methoxy-α-methylbenzylamine,
N-(4-benzyloxybenzyl)-α,β-diphenylethylamine,
N-(4-benzyloxybenzyl)-1-phenyl-2(p-tolyl)ethylamine,
N-(4-benzyloxybenzyl)-α-phenyl-β-(3-methoxyphenyl)ethylamine,
N-(4-benzyloxybenzyl)-α-phenyl-β-(4-chlorophenyl)ethylamine,
N-(4-benzyloxybenzyl)-α,γ-diphenylpropylamine,
N-(4-benzyloxybenzyl)-α-methyl-1-naphthylamine,
N-(4-benzyloxybenzyl)-α-methyl-2-naphthylmethylamine, and salts thereof with an inorganic acid such as hydrochloric acid, sulfuric acid, nitric acid or the like.

Preferred are optically active amine compounds of formula (4), wherein $R_{11}$ is a phenyl group and $R_{21}$ is a methyl group, and optically active amine compounds of formula (4), wherein $R_{11}$ is a 2,4-dichlorophenyl group and $R_{21}$ is a methyl group.

The optically active amine compound (4) can be obtained, for example, by a process, which comprises subjecting the imine compound of formula (7) to a reduction reaction.

In the imine compound of formula (7), $R_{11}$, $R_{21}$ and $R_{31}$ are as defined above for the optically active amine compound of formula (4).

Specific examples of the imine compound (7) include:

N-(3-benzyloxybenzylidene)-α-methylbenzylamine,
N-(3-benzyloxybenzylidene)-α-ethylbenzylamine,
N-(3-benzyloxybenzylidene)-α-propylbenzylamine,
N-(3-benzyloxybenzylidene)-α-isopropylbenzylamine,
N-(3-benzyloxybenzylidene)-α, 4-dimethylbenzylamine,
N-(3-benzyloxybenzylidene)-α-2,5-trimethylbenzylamine,
N-(3-benzyloxybenzylidene)-α, 2,4,6-tetramethylbenzylamine,
N-(3-benzyloxybenzylidene)-α-methyl-4-isopropylbenzylamine,
N-(3-benzyloxybenzylidene)-2-fluoro-α-methylbenzylamine,
N-(3-benzyloxybenzylidene)-3-fluoro-α-methylbenzylamine,
N-(3-benzyloxybenzylidene)-4-fluoro-α-methylbenzylamine,
N-(3-benzyloxybenzylidene)-4-bromo-α-methylbenzylamine,
N-(3-benzyloxybenzylidene)-2-chloro-α-methylbenzylamine, N-(3-benzyloxybenzylidene)-3-chloro-α-methylbenzylamine,
N-(3-benzyloxybenzylidene)-4-chloro-α-methylbenzylamine,
N-(3-benzyloxybenzylidene)-2,3-dichloro-α-methylbenzylamine,
N-(3-benzyloxybenzylidene)-2,4-dichloro-α-methylbenzylamine,
N-(3-benzyloxybenzylidene)-2-methoxy-α-methylbenzylamine,
N-(3-benzyloxybenzylidene)-4-methoxy-α-methylbenzylamine,
N-(3-benzyloxybenzylidene)-2-ethoxy-α-methylbenzylamine,
N-(3-benzyloxybenzylidene)-3,4-dimethoxy-α-methylbenzylamine,
N-(3-benzyloxybenzylidene)-5-fluoro-α-methylbenzylamine,
N-(3-benzyloxybenzylidene)-α, β-diphenylethylamine,
N-(3-benzyloxybenzylidene)-1-phenyl-2-(p-tolyl)ethylamine,
N-(3-benzyloxybenzylidene)-α-phenyl-β-(3-methoxyphenyl)ethylamine,
N-(3-benzyloxybenzylidene)-α-phenyl-β-(4-chlorophenyl)ethylamine,
N-(3-benzyloxybenzylidene)-α,γ-diphenylpropylamine,
N-(3-benzyloxybenzylidene)-α-methyl-1-naphthylamine,
N-(3-benzyloxybenzylidene)-α-methyl-2-naphthylmethylamine,
N-(4-benzyloxybenzylidene)-α-methylbenzylamine,
N-(4-benzyloxybenzylidene)-α-ethylbenzylamine,
N-(4-benzyloxybenzylidene)-α-propylbenzylamine,
N-(4-benzyloxybenzylidene)-α-isopropylbenzylamine,
N-(4-benzyloxybenzylidene)-α,4-dimethylbenzylamine,
N-(4-benzyloxybenzylidene)-α,2,5-trimethylbenzylamine,
N-(4-benzyloxybenzylidene)-α,2,4,6-tetramethylbenzylamine,
N-(4-benzyloxybenzylidene)-α-methyl-4-isopropylbenzylamine,
N-(4-benzyloxybenzylidene)-2-fluoro-α-methylbenzylamine,
N-(4-benzyloxybenzylidene)-3-fluoro-α-methylbenzylamine,
N-(4-benzyloxybenzylidene)-4-fluoro-α-methylbenzylamine,
N-(4-benzyloxybenzylidene)-4-bromo-α-methylbenzylamine,
N-(4-benzyloxybenzylidene)-2-chloro-α-methylbenzylamine,
N-(4-benzyloxybenzylidene)-3-chloro-α-methylbenzylamine,
N-(4-benzyloxybenzylidene)-4-chloro-α-methylbenzylamine,
N-(4-benzyloxybenzylidene)-2,3-dichloro-α-methylbenzylamine,
N-(4-benzyloxybenzylidene)-2,4-dichloro-α-methylbenzylamine,
N-(4-benzyloxybenzylidene)-2-methoxy-α-methylbenzylamine,
N-(4-benzyloxybenzylidene)-4-methoxy-α-methylbenzylamine,
N-(4-benzyloxybenzylidene)-2-ethoxy-α-methylbenzylamine,
N-(4-benzyloxybenzylidene)-3,4-dimethoxy-α-methylbenzylamine,
N-(4-benzyloxybenzylidene)-5-fluoro-2-methoxy-α-methylbenzylamine,
N-(4-benzyloxybenzylidene)-α,β-diphenylethylamine,
N-(4-benzyloxybenzylidene)-1-phenyl-2-(p-tolyl)ethylamine,
N-(4-benzyloxybenzylidene)-α-phenyl-β-(3-methoxyphenyl)ethylamine,
N-(4-benzyloxybenzylidene)-α-phenyl-β-4-chlorophenyl)ethylamine,
N-(4-benzyloxybenzylidene)-α, γ-diphenylpropylamine,
N-(4-benzyloxybenzylidene)- α-methyl-1-naphthylamine,
N-(4-benzyloxybenzylidene)-α-methyl-2-naphthylmethylamine and the like.

The reduction reaction is usually conducted, for example, by a process which comprises reacting the imine compound of formula (7) with a reducing agent such as a metal hydride or the like, alternatively with hydrogen in the presence of a catalyst.

Examples of the metal hydride include lithium aluminum hydride, sodium borohydride and borane and the like. Borane includes diborane, borane-THF, a borane-sulfide complex, a borane-amine complex and the like.

The amount of the reducing agent to be used is usually within the range of approximately from 0.25 to 5 moles, preferably approximately from 0.25 to 2 moles per mol of the imine compound (7) in the case where lithium aluminum hydride or sodium borohydride is used.

When borane is used, the amount of borane to be used, on a borone basis, is usually within the range of approximately from 0.3 to 5 moles, preferably approximately from 0.3 to 3 moles per mol of the imine compound (7).

The reduction reaction is usually conducted in an inert solvent. Examples of the inert solution include ethers such as diethyl ether, t-butyl methyl ether, n-butyl ether, tetrahydrofuran or the like, aromatic hydrocarbons such as benzene, toluene, xylene or the like, halogenated hydrocarbons such as chloroform, dichloromethane, dichloroethane, chlorobenzene or the like.

When sodium borohydride is used as a reducing agent, a lower alcohol such as methanol, ethanol, isopropyl alcohol or the like as well as the aforementioned solvents. The solvent may be used alone or as a mixture thereof. The amount of the solvent to be used is not particularly limited.

The reaction is usually conducted within a temperature range of approximately of from −50° C. to 100° C., preferably from −20° C. to 100° C.

After completion of the reaction, the optically active amine compound (4) is usually obtained, for example, by treating the resulting reaction mixture with water, acetic acid or an inorganic acid, and then extracted with a hydrophobic organic solvent under alkaline conditions, which was made by adding an appropriate amount of a base, phase separation of the organic phase and concentration thereof under a neutral or weakly basic condition. The product may be further purified by recrystallization, and/or column chromatography using silica gel, etc., if necessary.

Examples of the catalyst to be used for hydrogenation include Raney nickel, palladium-carbon, platinum dioxide, platinum black and the like.

The amount of such a catalyst to be used is usually from 0.1 to 100% by weight, preferably from 0.5 to 50% by weight per 1part by weight of the imine compound (7).

An inert solvent may be used in the hydrogenation reaction. Examples of the solvent include alcohols such as methanol, ethanol, isopropyl alcohol or the like, ethers such as diethyl ether, t-butyl methyl ether, n-butyl ether, tetrahydrofuran or the like, esters such as ethyl acetate, aromatic hydrocarbons such as benzene, toluene, xylene or the like, water, etc. These solvents may be used alone or as a mixture thereof. The amount of the solvent to be used is not particularly limited.

The hydrogenation is usually conducted within the range of approximately from −30° C. to 150° C., preferably from −10° C. to 100° C.

The hydrogenation is usually conducted at a pressure of approximately from 0 to 10 MPa (0 to 100 kg/cm$^2$), preferably approximately from 0 to 5 MPa (0 to 50 kg/cm$^2$).

After completion of the reaction, the optically active amine compound (4) can be obtained, for example, by removing the catalyst by filtration, followed by concentrating the filtrate. The desired product may be further purified by recrystallization and/or column chromatography using silica gel, if necessary.

The imine compound (7) is usually obtained by a process, which comprises reacting the optically active amine (5) with the benzyloxybenzaldehyde (6).

In the optically active amine (5), $R_{11}$ and $R_{21}$ are as defined above for the optically active compound of formula (4).

Examples of the optically active amine (5) include optical isomers of α-methylbenzylamine, 1-(1-naphthyl)ethylamine, α,4-dimethylbenzylamine, 4-isopropyl-α-methylbenzylamine, 4-nito-α-methylbenzylamine, 4-bromo-α-methylbenzylamine, α-ethylbenzylamine, α-isopropylbenzylamine, 1-phenyl-2-(p-tolyl)ethylamine and the like. These amines are commercially available or can be readily obtained by a known method. Alternatively, the optically active amine (5) can be obtained by a similar manner as disclosed in a reference such as Houben-Weyl, Methoden der Organischen Chemie, Georg-Thieme-Verlag, Stuttgart and the like.

Examples of the benzyloxybenzaldehyde of formula (6): $R_{31}$-CHO include 3-benzyloxybenzaldehyde and 4-benzyloxybenzaldehyde. These aldehydes are commercially available.

The optically active amine (5) is usually reacted with the benzyloxybenzaldehyde of formula (6) in a solvent. Examples of the solvent include alcohols such as methanol, ethanol, isopropyl alcohol or the like, ethers such as diethyl ether, t-butyl methyl ether, n-butyl ether, tetrahydrofuran or the like, aromatic hydrocarbons such as benzene, toluene, xylene or the like, halogenated hydrocarbons such as chloroform, dichloromethane, dichloroethane, chlorobenzene or the like.

The solvent may be used alone or as a mixture thereof.

The amount of the benzyloxybenzaldehyde (6) is usually 1 to 1.2 moles per mole of the optically active amine (5).

The reaction temperature is usually within the range of from 0° C. to 200° C., preferably from 0° C. to 150° C.

Although the obtained imine compound (7) can be isolated by evaporation and the like, it may be used in the subsequent reaction as it is without being isolated.

Next description will be made to the optically active amine compound of formula (8) as defined above, a process for producing the same, the imine compound (11) and processes of using and producing the same.

In the novel optically active compound of formula (8), the halogen atom represented by $X_1$ to $X_5$ have the same meanings as defined above.

The lower alkyl group represented by $R_{22}$ or $X_2$ to $X_5$ include a C1–C4 alkyl group as specified for $R_2$ above.

Preferably, $X_1$ and $X_3$ represent halogen atoms such as chlorine and $X_2$, $X_4$ and $X_5$ represent hydrogen atoms.

The lower alkyl group and the lower alkoxy group on the aryl group in $R_{32}$ include C1–$C_4$ alkyl group and C1–C4 alkoxy group respectively.

Examples of the aryl group include C6–C10 aryl group such as a phenyl or naphthyl group.

Examples of the C6–C10 aryl group substituted with at least one group selected from a C1–C4 alkyl group, a C1–C4 alkoxy group, an aryl group (e.g. a phenyl or naphthyl group) and an aryloxy group (e.g. a phenoxy or naphthoxy group), in $R_{32}$ include a 1-maphthyl group, a 2-naphthyl group, a 4-methylphenyl group, a 4-ethylpehnyl group, a 4-propylphenyl group, a 4-isopropylphenyl group, a 4-t-butylphenyl group, a 2,5-dimethylphenyl group, a 2,4,6-trimethylphenyl group, a 2-methoxyphenyl group, a 4-methoxyphenyl group, a 2-ethoxyphenyl group, a 2-propoxyphenyl group, a 3,4-dimethoxyphenyl group, a 3-phenoxyphenyl group, and a 4-phenylphenyl group. Among these groups, preferred are 3-phenoxypehnyl group and a 4-phenylphenyl group.

Specific examples the optically active amine compound of formula (8) or salts thereof include optically active isomers of N-(4-methylbenzyl)-2-chloro-α-methylbenzylamine, N-(2,5-dimethylbenzyl)-2-chloro-α-methylbenzylamine, N-(2,4,6-trimethylbenzyl)-2-chloro-α-methylbenzylamine, N-(4-isopropylbenzyl)-2-chloro-α-methylbenzylamine, N-(2-methoxylbenzyl)-2-chloro-α-methylbenzylamine, N-(4-methoxylbenzyl)-2-chloro-α-methylbenzylamine, N-(2-ethoxylbenzyl)-2-chloro-α-methylbenzylamine, N-(3,4-dimethoxylbenzyl)-2-chloro-α-methylbenzylamine, N-(3-phenoxybenzyl)-2-chloro-α-methylbenzylamine, N-(4-phenoxybenzyl)-2-chloro-α-methylbenzylamine, N-(2-phenylbenzyl)-2-chloro-α-methylbenzylamine, N-(3-phenylbenzyl)-2-chloro-α-methylbenzylamine, N-(4-phenylbenzyl)-2-chloro-α-methylbenzylamine, N-(4-methylbenzyl)-2,3-dichloro-α-methylbenzylamine, N-(2,5-dimethylbenzyl)-2,3-dichloro-α-methylbenzylamine, N-(2,4,6-trimethylbenzyl)-2,3-dichloro-α-methylbenzylamine, N-(4-isopropylbenzyl)-2,3-dichloro-α-methylbenzylamine, N-(2-methoxyylbenzyl)-2,3-dichloro-α-methylbenzylamine, N-(4-methoxylbenzyl)-2,3-dichloro-α-methylbenzylamine, N-(2-ethoxylbenzyl)-2,3-dichloro-α- methylbenzylamine, N-(3,4-dimethoxylbenzyl)-2,3-dichloro-α-methylbenzylamine, N-(3-phenoxybenzyl)-2,3-dichloro-α-methyl-benzylamine,
N-(4-phenoxybenzyl)-2,3-dichloro-α-methyl-benzylamine,
N-(2-phenoxybenzyl)-2,3-dichloro-α-methyl-benzylamine,
N-(3-phenoxybenzyl)-2,3-dichloro-α-methyl-benzylamine,
N-(4-phenoxybenzyl)-2,3-dichloro-α-methyl-benzylamine, N-(4-methylbenzyl)-2,4-dichloro-α-methylbenzylamine,
N-(2,5-dimethylbenzyl)-2,4-dichloro-α-methyl-benzylamine,
N-(2,4,6-trimethylbenzyl)-2,4-dichloro-α-methylbenzylamine,
N-(4-isopropylbenzyl)-2,4-dichloro-α-methyl-benzylamine,
N-(2-methoxylbenzyl)-2,4-dichloro-α-methyl-benzylamine,
N-(4-methoxylbenzyl)-2,4-dichloro-α-methyl-benzylamine,
N-(2-ethoxylbenzyl)-2,4-dichloro-α-methylbenzylamine,
N-(3,4-dimethoxylbenzyl)-2,4-dichloro-α-methylbenzylamine,
N-(3-phenoxybenzyl)-2,4-dichloro-α-methyl-benzylamine,
N-(4-phenoxybenzyl)-2,4-dichloro-α-methyl-benzylamine,
N-(2-phenylbenzyl)-2,4-dichloro-α-methylbenzylamine,
N-(3-phenylbenzyl)-2,4-dichloro-α-methylbenzylamine,
N-(4-phenylbenzyl)-2,4-dichloro-α-methylbenzylamine, N-(4-methylbenzyl)-2,5-dichloro-α-methylbenzylamine,
N-(2,5-dimethylbenzyl)-2,5-dichloro-α-methyl-benzylamine,
N-(2,4,6-trimethylbenzyl)-2,5-dichloro-α-methylbenzylamine,
N-(4-isopropylbenzyl)-2,5-dichloro-α-methyl-benzylamine,
N-(2-methoxylbenzyl)-2,5-dichloro-α-methyl-benzylamine,
N-(4-methoxylbenzyl)-2,5-dichloro-α-methyl-benzylamine,
N-(2-ethoxylbenzyl)-2,5-dichloro-α-methylbenzylamine,
N-(3,4-dimethoxylbenzyl)-2,5-dichloro-α-methylbenzylamine,
N-(3-phenoxybenzyl)-2,5-dichloro-α-methyl-benzylamine,
N-(4-phenoxybenzyl)-2,5-dichloro-α-methyl-benzylamine,
N-(2-phenylbenzyl)-2,5-dichloro-α-methylbenzylamine,
N-(3-phenylbenzyl)-2,5-dichloro-α-methylbenzylamine,
N-(4-phenylbenzyl)-2,5-dichloro-α-methylbenzylamine, N-(4-methylbenzyl)-2,6-dichloro-α-methylbenzylamine,
N-(2,5-dimethylbenzyl)-2,6-dichloro-α-methyl-benzylamine,
N-(2,4,6-trimethylbenzyl)-2,6-dichloro-α-methylbenzylamine,
N-(4-isopropylbenzyl)-2,6-dichloro-α-methyl-benzylamine,
N-(2-methoxylbenzyl)-2,6-dichloro-α-methyl-benzylamine,
N-(4-methoxylbenzyl)-2,6-dichloro-α-methyl-benzylamine,
N-(2-ethoxylbenzyl)-2,6-dichloro-α-methylbenzylamine,
N-(3,4-dimethoxylbenzyl)-2,6-dichloro-α-methylbenzylamine,
N-(3-phenoxybenzyl)-2,6-dichloro-α-methyl-benzylamine,
N-(4-phenoxybenzyl)-2,6-dichloro-α-methyl-benzylamine,
N-(2-phenylbenzyl)-2,6-dichloro-α-methylbenzylamine,
N-(3-phenylbenzyl)-2,6-dichloro-α-methylbenzylamine,
N-(4-phenylbenzyl)-2,6-dichloro-α-methylbenzylamine, N-(4-methylbenzyl)-2,4,6-trichloro-α-methyl-benzylamine,
N-(2,5-dimethylbenzyl)-2,4,6-trichloro-α-methylbenzylamine,
N-(2,4,6-trimethylbenzyl)-2,4,6-trichloro-α-methylbenzylamine,
N-(4-isopropylbenzyl)-2,4,6-trichloro-α-methylbenzylamine,
N-(2-methoxylbenzyl)-2,4,6-trichloro-α-methylbenzylamine,
N-(4-methoxylbenzyl)-2,4,6-trichloro-α-methylbenzylamine,
N-(2-ethoxylbenzyl)-2,4,6-trichloro-α-methyl-benzylamine,
N-(3,4-dimethoxylbenzyl)2,4,6-trichloro-α-methylbenzylamine,
N-(3-phenoxybenzyl)-2,4,6-trichloro-α-methyl-benzylamine,
N-(4-phenoxybenzyl)-2,4,6-trichloro-α-methyl-benzylamine,
N-(2-phenylbenzyl)-2,4,6-trichloro-α-methyl-benzylamine,
N-(3-phenylbenzyl)-2,4,6-trichloro-α-methyl-benzylamine,
N-(4-phenylbenzyl)-2,4,6-trichloro-α-methyl-benzylamine, N-(4-methylbenzyl)-2,3,4-trichloro-α-methyl-benzylamine,
N-(2,5-dimethylbenzyl)-2,3,4-trichloro-α-methylbenzylamine,
N-(2,4,6-trimethylbenzyl)-2,3,4-trichloro-α-methylbenzylamine,
N-(4-isopropylbenzyl)-2,3,4-trichloro-α-methylbenzylamine,
N-(2-methoxylbenzyl)-2,3,4-trichloro-α-methylbenzylamine,
N-(4-methoxylbenzyl)-2,3,4-trichloro-α-methylbenzylamine,
N-(2-ethoxylbenzyl)-2,3,4-trichloro-α-methyl-benzylamine,
N-(3,4-dimethoxylbenzyl)-2,3,4-trichloro-α-methylbenzylamine,
N-(3-phenoxybenzyl)-2,3,4-trichloro-α-methyl-benzylamine,
N-(4-phenoxybenzyl)-2,3,4-trichloro-α-methyl-benzylamine, N-(2-phenylbenzyl)-2,3,4-trichloro-α-methylbenzylamine,
N-(3-phenylbenzyl)-2,3,4-trichloro-α-methylbenzylamine,
N-(4-phenylbenzyl)-2,3,4-trichloro-α-methylbenzylamine, N-(4-methylbenzyl)-2,4-difluoro-α-methylbenzylamine,
N-(2,5-dimethylbenzyl)-2,4-difluoro-α-methylbenzylamine,
N-(2,4,6-trimethylbenzyl)-2,4-difluoro-α-methylbenzylamine,
N-(4-isopropylbenzyl)-2,4-difluoro-α-methylbenzylamine,
N-(2-methoxylbenzyl)-2,4-difluoro-α-methylbenzylamine,
N-(4-methoxylbenzyl)-2,4-difluoro-α-methylbenzylamine,
N-(2-ethoxylbenzyl)-2,4-difluoro-α-methylbenzylamine,
N-(3,4-dimethoxylbenzyl)-2,4-difluoro-α-methylbenzylamine,
N-(3-phenoxybenzyl)-2,4-difluoro-α-methylbenzylamine,
N-(4-phenoxybenzyl)-2,4-difluoro-α-methylbenzylamine,
N-(2-phenylbenzyl)-2,4-difluoro-α-methylbenzylamine,
N-(3-phenylbenzyl)-2,4-difluoro-α-methylbenzylamine,
N-(4-phenylbenzyl)-2,4-difluoro-α-methylbenzylamine, N-(4-methylbenzyl)-2,4-dibromo-α-methylbenzylamine,
N-(2,5-dimethylbenzyl)-2,4-dibromo-α-methylbenzylamine,
N-(2,4,6-trimethylbenzyl)-2,4-dibromo-αmethylbenzylamine,
N-(4-isopropylbenzyl)-2,4-dibromo-α-methylbenzylamine,
N-(2-methoxylbenzyl)-2,4-dibromo-αmethylbenzylamine,
N-(4-methoxylbenzyl)-2,4-dibromo-α-methylbenzylamine,
N-(2-ethoxylbenzyl)-2,4-dibromo-α-methylbenzylamine,
N-(3,4-dimethoxylbenzyl)-2,4-dibromo-α-methylbenzylamine,
N-(3-phenoxybenzyl)-2,4-dibromo-α-methylbenzylamine,
N-(4-phenoxybenzyl)-2,4-dibromo-α-methylbenzylamine,
N-(2-phenylbenzyl)-2,4-dibromo-α-methylbenzylamine,
N-(3-phenylbenzyl)-2,4-dibromo-α-methylbenzylamine,
N-(4-phenylbenzyl)-2,4-dibromo-α-methylbenzylamine, N-(4-methylbenzyl)-2,4-diiodo-α-methylbenzylamine,
N-(2,5-dimethylbenzyl)2,4-diiodo-α-methylbenzylamine,
N-(2,4,6-trimethylbenzyl)-2,4-diiodo-α-methylbenzylamine,
N-(4-isopropylbenzyl)-2,4-diiodo-α-methylbenzylamine,
N-(2-methoxylbenzyl)-2,4-diiodo-α-methylbenzylamine,
N-(4-methoxylbenzyl)-2,4-diiodo-αmethylbenzylamine,
N-(2-ethoxylbenzyl)-2,4-diiodo-α-methylbenzylamine,
N-(3,4-dimethoxylbenzyl)-2,4-diiodo-α-methylbenzylamine,
N-(3-phenoxybenzyl)2,4-diiodo-α-methylbenzylamine,
N-(4-phenoxybenzyl)-2,4-diiodo-α-methylbenzylamine,
N-(2-phenylbenzyl)-2,4-diiodo-α-methylbenzylamine,
N-(3-phenylbenzyl)-2,4-diiodo-α-methylbenzylamine,
N-(4-phenylbenzyl)-2,4-diiodo-α-methylbenzylamine, N-(4-methylbenzyl)-2,4-dimethyl-α-methylbenzylamine,
N-(2,5-dimethylbenzyl)-2,4-dimethyl-α-methylbenzylamine,
N-(2,4,6-trimethylbenzyl)-2,4-dimethyl-α-methylbenzylamine,
N-(4-isopropylbenzyl)-2,4-dimethyl-α-methylbenzylamine,
N-(2-methoxylbenzyl)-2,4-dimethyl-α-methylbenzylamine,
N-(4-methoxylbenzyl)-2,4-dimethyl-α-methylbenzylamine,
N-(2-ethoxylbenzyl)-2,4-dimethyl-α-methylbenzylamine,
N-(3,4-dimethoxylbenzyl)-2,4-dimethyl-α-methylbenzylamine,
N-(3-phenoxybenzyl)-2,4-dimethyl-α-methylbenzylamine,
N-(4-phenoxybenzyl)-2,4-dimethyl-α-methylbenzylamine,
N-(2-phenylbenzyl)-2,4-dimethyl-α-methylbenzylamine,
N-(3-phenylbenzyl)-2,4-dimethyl-α-methylbenzylamine,
N-(4-phenylbenzyl)-2,4-dimethyl-α-methylbenzylamine, N-(4-methylbenzyl)-2,4-diethyl-α-methylbenzylamine,
N-(2,5-dimethylbenzyl)-2,4-diethyl-α-methylbenzylamine,
N-(2,4,6trimethylbenzyl)-2,4-diethyl-α-methylbenzylamine,
N-(4-isopropylbenzyl)-2,4-diethyl-α-methylbenzylamine,
N-(2-methoxylbenzyl)-2,4-diethyl-α-methylbenzylamine,
N-(4-methoxylbenzyl)-2,4-diethyl-α-methylbenzylamine,
N-(2-ethoxylbenzyl)-2,4-diethyl-α-methylbenzylamine,
N-(3,4-dimethoxylbenzyl)-2,4-diethyl-α-methylbenzylamine,
N-(3-phenoxybenzyl)-2,4-diethyl-α-methylbenzylamine,
N-(4-phenoxybenzyl)-2,4-diethyl-α-methylbenzylamine,
N-(2-phenylbenzyl)-2,4-diethyl-α-methylbenzylamine,
N-(3-phenylbenzyl)-2,4-diethyl-α-methylbenzylamine,
N-(4-phenylbenzyl)-2,4-diethyl-α-methylbenzylamine,
and salts thereof with an inorganic acid such as hydrochloric acid, sulfuric acid, nitric acid or the like.

The optically active amine compound of formula (8) can be, for example, obtained by a process, which comprises subjecting the imine compound of formula (11) to a reduction reaction.

In the imine compound of formula (11), $X_1$ to $X_5$, $R_{22}$ and $R_{32}$ respectively have the same meanings as defined for the optically active amine compound of formula (8) above.

Specific examples of the imine compound (11) include:
N-(4-methylbenzylamine)-2-chloro-α-methylbenzylamine,
N-(2,5-dimethylbenzylamine)-2-chloro-α-methylbenzylamine, N-(2,4,6-trimethylbenzyl)-2-chloro-α-methylbenzylamine,
N-(4-isopropylbenzylamine)-2-chloro-α-methylbenzylamine,
N-(2-methoxylbenzylidene)-2-chloro-α-methylbenzylamine,
N-(4-methoxylbenzylidene)-2-chloro-α-methylbenzylamine,
N-(2-ethoxylbenzylidene)-2-chloro-α-methylbenzylamine,
N-(3,4-dimethoxylbenzylidene)-2-chloro-α-methylbenzylamine,
N-(3-phenoxybenzylidene)-2-chloro-α-methylbenzylamine,
N-(4-phenoxybenzylidene)-2-chloro-α-methylbenzylamine,
N-(2-phenylbenzylidene)-2-chloro-α-methylbenzylamine,
N-(3-phenylbenzylidene)-2-chloro-α-methylbenzylamine,
N-(4-phenylbenzylidene)-2-chloro-α-methylbenzylamine, N-(4-methylbenzylamine)-2,3-dichloro-α-methylbenzylamine,
N-(2,5-dimethylbenzylidene)-2,3-dichloro-α-methylbenzylamine,
N-(2,4,6-trimethylbenzylidene)-2,3-dichloro-α-methylbenzylamine,
N-(4-isopropylbenzylidene)-2,3-dichloro-α-methylbenzylamine,
N-(2-methoxylbenzylidene)-2,3-dichloro-α-methylbenzylamine,
N-(4-methoxylbenzylidene)-2,3-dichloro-α-methylbenzylamine,
N-(2-ethoxylbenzylidene)-2,3-dichloro-α-methylbenzylamine,
N-(3,4-dimethoxylbenzylidene)-2,3-dichloro-α-methylbenzylamine,
N-(3-phenoxybenzylidene)-2,3-dichloro-α-methylbenzylamine,
N-(4-phenoxybenzylidene)-2,3-dichloro-α-methylbenzylamine,
N-(2-phenylbenzylidene)-2,3-dichloro-α-methylbenzylamine,
N-(3-phenylbenzylidene)-2,3-dichloro-α-methylbenzylamine,
N-(4-phenylbenzylidene)-2,3-dichloro-α-methylbenzylamine, N-(4-methylbenzylidene)-2,4-dichloro-α-methylbenzylamine,
N-(2,5-dimethylbenzylidene)-2,4-dichloro-α-methylbenzylamine,
N-(2,4,6-trimethylbenzylidene)-2,4-dichloro-α-methylbenzylamine,
N-(4-isopropylbenzylidene)-2,4-dichloro-α-methylbenzylamine,
N-(2-methoxylbenzylidene)-2,4-dichloro-α-methylbenzylamine,
N-(4-methoxylbenzylidene)-2,4-dichloro-α-methylbenzylamine,
N-(2-ethoxylbenzylidene)-2,4-dichloro-α-methylbenzylamine,
N-(3,4-dimethoxylbenzylidene)-2,4-dichloro-α-methylbenzylamine,
N-(3-phenoxybenzylidene)-2,4-dichloro-α-methylbenzylamine,
N-(4-phenoxybenzylidene)-2,4-dichloro-α-methylbenzylamine,
N-(2-phenylbenzylidene)-2,4-dichloro-α-methylbenzylamine,
N-(3-phenylbenzylidene)-2,4-dichloro-α-methylbenzylamine,
N-(4-phenylbenzylidene)-2,4-dichloro-α-methylbenzylamine, N-(4-methylbenzylidene)-2,5-dichloro-α-methylbenzylamine,
N-(2,5-dimethylbenzylidene)-2,5-dichloro-α-methylbenzylamine,
N-(2,4,6-trimethylbenzylidene)-2,5-dichloro-α-methylbenzylamine,
N-(4-isopropylbenzylidene)-2,5-dichloro-α-methylbenzylamine,
N-(2-methoxylbenzylidene)-2,5-dichloro-α-methylbenzylamine,
N-(4-methoxylbenzylidene)-2,5-dichloro-α-methylbenzylamine,
N-(2-ethoxylbenzylidene)-2,5-dichloro-α-methylbenzylamine,
N-(3,4-dimethoxylbenzylidene)-2,5-dichloro-α-methylbenzylamine,
N-(3-phenoxybenzylidene)-2,5-dichloro-α-methylbenzylamine,
N-(4-phenoxybenzylidene)-2,5-dichloro-α-methylbenzylamine,
N-(2-phenylbenzylidene)-2,5-dichloro-α-methylbenzylamine,
N-(3-phenylbenzylidene)-2,5-dichloro-α-methylbenzylamine,
N-(4-phenylbenzylidene)-2,5-dichloro-α-methylbenzylamine, N-(4-methylbenzylidene)-2,6-dichloro-α-methylbenzylamine,
N-(2,5-dimethylbenzylidene)-2,6-dichloro-α-methylbenzylamine,
N-(2,4,6-trimethylbenzylidene)-2,6-dichloro-α-methylbenzylamine,
N-(2-methoxylbenzylidene)-2,6-dichloro-α-methylbenzylamine,
N-(4-methoxylbenzylidene)-2,6-dichloro-α-methylbenzylamine,
N-(2-ethoxylbenzylidene)-2,6-dichloro-α-methylbenzylamine,
N-(3,4-dimethoxylbenzylidene)-2,6-dichloro-α-methylbenzylamine,
N-(3-phenoxybenzylidene)-2,6-dichloro-α-methylbenzylamine,
N-(4-phenoxybenzylidene)-2,6-dichloro-α-methylbenzylamine,
N-(2-phenylbenzylidene)-2,6-dichloro-α-methylbenzylamine, N-(3-phenylbenzylidene)-2,6-dichloro-α-methylbenzylamine, N-(4-phenylbenzylidene)-2,6-dichloro-α-methylbenzylamine, N-(4-methylbenzylidene)-2,4,6-trichloro-α-methylbenzylamine, N-(2,5-dimethylbenzylidene)-2,4,6-trichloro-α-methylbenzylamine, N-(2,4,6-trimethylbenzylidene)-2,4,6-trichloro-α-methylbenzylamine, N-(4-isopropylbenzylidene)-2,4,6-trichloro-α-methylbenzylamine, N-(2-methoxylbenzylidene)-2,4,6-trichloro-α-methylbenzylamine, N-(4-methoxylbenzylidene)-2,4,6-trichloro-α-methylbenzylamine, N-(2-ethoxylbenzylidene)-2,4,6-trichloro-α-methylbenzylamine, N-(3,4-dimethoxylbenzylidene)-2,4,6-trichloro-α-methylbenzylamine, N-(3-phenoxybenzylidene)-2,4,6-trichloro-α-methylbenzylamine, N-(4-phenoxybenzylidene)-2,4,6-trichloro-α-methylbenzylamine, N-(2-phenylbenzylidene)-2,4,6-trichloro-α-methylbenzylamine, N-(3-phenylbenzylidene)-2,4,6-trichloro-α-methylbenzylamine, N-(4-phenylbenzylidene)-2,4,6-trichloro-α-methylbenzylamine, N-(4-methylbenzylidene)-2,3,4-trichloro-α-methylbenzylamine, N-(2,5-dimethylbenzylidene)-2,3,4-trichloro-α-methylbenzylamine, N-(2,4,6-trimethylbenzylidene)-2,3,4-trichloro-α-methylbenzylamine, N-(4-isopropylbenzylidene)-2,3,4-trichloro-α-methylbenzylamine, N-(2-methoxylbenzylidene)-2,3,4-trichloro-α-methylbenzylamine, N-(4-methoxylbenzylidene)-2,3,4-trichloro-α-methylbenzylamine, N-(2-ethoxylbenzylidene)-2,3,4-trichloro-α-methylbenzylamine, N-(3,4-dimethoxylbenzylidene)-2,3,4-trichloro-α-methylbenzylamine, N-(3-phenoxybenzylidene)-2,3,4-trichloro-α-methylbenzylamine, N-(4-phenoxybenzylidene)-2,3,4-trichloro-α-methylbenzylamine, N-(2-phenylbenzylidene)-2,3,4-trichloro-α-methylbenzylamine, N-(3-phenylbenzylidene)-2,3,4-trichloro-α-methylbenzylamine, N-(4-phenylbenzylidene)-2,3,4-trichloro-α-methylbenzylamine, N-(4-methylbenzylidene)-2,4-difluoro-α-methylbenzylamine, N-(2,5-dimethylbenzylidene)-2,4-difluoro-α-methylbenzylamine, N-(2,4,6-trimethylbenzylidene)-2,4-difluoro-α-methylbenzylamine, N-(4-isopropylbenzylidene)-2,4-difluoro-α-methylbenzylamine, N-(2-methoxylbenzylidene)-2,4-difluoro-α-methylbenzylamine, N-(4-methoxylbenzylidene)-2,4-difluoro-α-methylbenzylamine, N-(2-ethoxylbenzylidene)-2,4-difluoro-α-methylbenzylamine, N-(3,4-dimethoxylbenzylidene)-2,4-difluoro-α-methylbenzylamine, N-(3-phenoxybenzylidene)-2,4-difluoro-α-methylbenzylamine, N-(4-phenoxybenzylidene)-2,4-difluoro-α-methylbenzylamine, N-(2-phenylbenzylidene)-2,4-difluoro-α-methylbenzylamine, N-(3-phenylbenzylidene)-2,4-difluoro-α-methylbenzylamine, N-(4-phenylbenzylidene)-2,4-difluoro-α-methylbenzylamine, N-(4-methylbenzylidene)-2,4-dibromo-α-methylbenzylamine, N-(2,5-dimethylbenzylidene)-2,4-dibromo-α-methylbenzylamine, N-(2,4,6-trimethylbenzylidene)-2,4-dibromo-α-methylbenzylamine, N-(4-isopropylbenzylidene)-2,4-dibromo-α-methylbenzylamine, N-(2-methoxylbenzylidene)-2,4-dibromo-α-methylbenzylamine, N-(4-methoxylbenzylidene)-2,4-dibromo-α-methylbenzylamine, N-(2-ethoxylbenzylidene)-2,4-dibromo-α-methylbenzylamine, N-(3,4-dimethoxylbenzylidene)-2,4-dibromo-α-methylbenzylamine, N-(3-phenoxybenzylidene)-2,4-dibromo-α-methylbenzylamine, N-(4-phenoxybenzylidene)-2,4-dibromo-α-methylbenzylamine, N-(2-phenylbenzylidene)-2,4-dibromo-α-methylbenzylamine, N-(3-phenylbenzylidene)-2,4-dibromo-α-methylbenzylamine, N-(4-phenylbenzylidene)-2,4-dibromo-α-methylbenzylamine, N-(4-methylbenzylidene)-2,4-diiodo-α-methylbenzylamine, N-(2,5-dimethylbenzylidene)-2,4-diiodo-α-methylbenzylamine, N-(2,4,6-trimethylbenzylidene)-2,4-diiodo-α-methylbenzylamine, N-(4-isopropylbenzylidene)-2,4-diiodo-α-methylbenzylamine, N-(2-methoxylbenzylidene)-2,4-diiodo-α-methylbenzylamine, N-(4-methoxylbenzylidene)-2,4-diiodo-α-methylbenzylamine, N-(2-ethoxylbenzylidene)-2,4-diiodo-α-methyl-benzylamine,
N-(3,4-dimethoxylbenzylidene)-2,4-diiodo-α-methylbenzylamine,
N-(3-phenoxybenzylidene)-2,4-diiodo-α-methylbenzylamine,
N-(4-phenoxybenzylidene)-2,4-diiodo-α-methylbenzylamine,
N-(2-phenylbenzylidene)-2,4-diiodo-α-methylbenzylamine,
N-(3-phenylbenzylidene)-2,4-diiodo-α-methylbenzylamine,
N-(4-phenylbenzylidene)-2,4-diiodo-α-methylbenzylamine, N-(4-methylbenzylidene)-2,4-dimethyl-α-methylbenzylamine,
N-(2,5-dimethylbenzylidene)-2,4-dimethyl-α-methylbenzylamine,
N-(2,4,6-trimethylbenzylidene)-2,4-dimethyl-α-methylbenzylamine,
N-(4-isopropylbenzylidene)-2,4-dimethyl-α-methylbenzylamine,
N-(2-methoxylbenzylidene)-2,4-dimethyl-α-methylbenzylamine,
N-(4-methoxylbenzylidene)-2,4-dimethyl-α-methylbenzylamine,
N-(2-ethoxylbenzylidene)-2,4-dimethyl-α-methylbenzylamine,
N-(3,4-dimethoxylbenzylidene)-2,4-dimethyl-α-methylbenzylamine,
N-(3-phenoxybenzylidene)-2,4-dimethyl-α-methylbenzylamine,
N-(4-phenoxybenzylidene)-2,4-dimethyl-α-methylbenzylamine,
N-(2-phenylbenzylidene)-2,4-dimethyl-α-methylbenzylamine,
N-(3-phenylbenzylidene)-2,4-dimethyl-α-methylbenzylamine,
N-(4-phenylbenzylidene)-2,4-dimethyl-α-methylbenzylamine, N-(4-methylbenzylidene)-2,4-diethyl-α-methylbenzylamine,
N-(2,5-dimethylbenzylidene)-2,4-diethyl-α-methylbenzylamine,
N-(2,4,6-trimethylbenzylidene)-2,4-diethyl-α-methylbenzylamine,
N-(4-isopropylbenzylidene)-2,4-diethyl-α-methylbenzylamine,
N-(2-methoxylbenzylidene)-2,4-diethyl-α-methylbenzylamine,
N-(4-methoxylbenzylidene)-2,4-diethyl-α-methylbenzylamine,
N-(2-ethoxylbenzylidene)-2,4-diethyl-α-methylbenzylamine,
N-(3,4-dimethoxylbenzylidene)-2,4-diethyl-α-methylbenzylamine,
N-(3-phenoxybenzylidene)-2,4-diethyl-α-methylbenzylamine,
N-(4-phenoxybenzylidene)-2,4-diethyl-α-methylbenzylamine,
N-(2-phenylbenzylidene)-2,4-diethyl-α-methylbenzylamine,
N-(3-phenylbenzylidene)-2,4-diethyl-α-methylbenzylamine,
N-(4-phenylbenzylidene)-2,4-diethyl-α-methylbenzylamine, The reduction reaction of the imine compound (11) is usually conducted by a process which comprises reacting the imine compound (11) with a reducing agent such as a metal hydride or the like, alternatively with hydrogen in the presence of a catalyst.

Examples of the metal hydride include lithium aluminum hydride, sodium borohydride and boronhydride and borane and the like. Borane includes diborane, borane-THF, a borane-sulfide complex, a borane-amine complex and the like.

The amount of the reducing agent to be used in usually within the range of approximately from 0.25 to 5 moles, preferably approximately from 0.25 to 2 moles per mol of the imine compound (11) in the case where lithium aluminum hydride or sodium borohydride is used.

When borane is used, the amount of borane to be used, on a borone basis, is usually within the range of approximately from 0.3 to 5 moles, preferably approximately from 0.3 to 3 moles per mol of the imine compound (11).

The reduction reaction is usually conducted in an inert solvent. Examples of the inert solvents include those as specified for the reduction reaction of the imine compound of formula (7) above.

When sodium borohydride is used as a reducing agent, a lower alcohol such as methanol, ethanol, isopropyl alcohol or the like can be used as well as the aforementioned solvents. The solvent may be used alone or as a mixture thereof. The amount of the solvent to be used is not particularly limited.

The reaction is usually conducted within a temperature range of approximately of from −50° C. to 100° C., preferably from −20 C. to 100° C.

After completion of the reaction, the optically active amine compound (8) is usually obtained, for example, by treating the resulting reaction mixture with water, acetic acid or a mineral acid, and then being made alkaline, followed by extraction with a hydrophobic organic solvent, phase separation of the organic phase and concentration thereof under a neutral or weakly basic condition. The product may be further purified by recrystallization, and/or column chromatography using silica gel, etc., if necessary.

Examples of the catalyst to be used for the reduction with hydrogen include Raney nickel, palladium-carbon, platinum dioxide, platinum black and the like.

The amount of such a catalyst to be used is usually from 0.1 to 100% by weight, preferably from 0.5 to 50% by weight per 1 part by weight of the imine compound (11).

The hydrogenation reaction in the presence of a catalyst is usually conducted in an inert solvent. Examples of the solvent include those as specified for the reduction reaction of the imine compound of formula (7) above. The amount of the solvent to be used is not particularly limited.

The hydrogenation is usually conducted within the range of approximately from −30° C. to 150° C., preferably from −10° C. to 100° C.

The hydrogenation is usually conducted at a pressure of approximately from 0 to 10 MPa (0 to100 kg/cm$^2$), preferably approximately from 0 to 5 MPa (0to 50 kg/cm$^2$).

After completion of the reaction, the optically active amine compound (8) can be obtained, for example, by removing the catalyst by filtration, followed by concentrating the filtrate. The desired product may be further purified by recrystallization and/or column chromatography using silica gel, if necessary.

Then imine compound of formula (11) can be obtained, for example, by a process which comprises reacting the aldehyde compound of formula (10) with an optically active amine compound of formula (9).

Examples of the aldehyde compound of formula (10) include 4-methylbenzaldehyde, 2,5-dimethylbenzylidene, 2,4,6-trimethylbenzylidene, 4-isopropylbenzylidene, 2-methoxybenzaldehyde, 4-methoxybenzaldehyde, 2-ethoxybenzaldehyde, 3,4-dimethyoxybenzaldehyde, 5-fluoro-2-methoxybenzaldehyde, 3-phenoxybenzaldehyde, 4-phenoxybenzaldehyde, 2-phenylbenzaldehyde, 3-phenylbenzaldehyde, 4-phenylbenzaldehyde, and the like. These aldehydes are commercially available or may be obtained by a similar manner as disclosed in references such as Houben-Weyl, Methoden der Organischen Chemie, Georg-Thieme-Verlag, Stuttgart and the like.

Examples of the optically active amine compound of formula (9) include 2,4-dichloro-α-methylbenzylamine and the like.

The optically active amine (9) is usually reacted with the benzaldehyde of formula (10) in a solvent. Examples of the solvent include those specified above for the reaction of the optically active amine compound of formula (5) with the benzyloxybenzaldehyde (6).

The optically active amine (9) are commercially available or can be obtained by a similar manner as disclosed in references such as Houben-Weyl, Methoden der Organischen Chemie, Georg-Thieme-Verlag, Stuttgart and the like.

The amount of the benzaldehyde (10) is usually 1 to 1.2 moles per mole of the optically active amine (9).

The reaction is usually conducted within the range of from 0° C. to 200° C., preferably from 0° C. to 150° C.

Although the obtained imine compound (11) can be isolated, for example, by evaporation and the like, it may be used, as it is, in the subsequent reaction without being isolated.

EXAMPLES

The present invention will be explained by the following examples, but it is not to be construed to limit the present invention thereto.

In the following examples, optical purities were determined by high performance liquid chromatography.

Example 1

In 2.96 g of t-butyl methyl ether, 148 mg (0.94 mmol) of racemic 3,3,3-trifluoro-2-hydroxy-2-methylpropioniic acid was dissolved at 55° C. To this solution was added, at that temperature, a solution prepared by dissolving in advance 136 mg (0.45 mmol) of (S)-N-benzyl-1-phenyl-2-(p-tolyl) ethylamine in 2.96 g of t-butyl methyl ether, and then stirred to mix.

After ascertaining the precipitation of crystals, the mixture was cooled gradually to 20° C. over 3 hours with stirring.

The crystals formed were collected by filtration, washed with 2.96 g of t-butyl methyl ether and then dried to yield 87 mg of (S)-N-benzyl-1-phenyl-2-(p-tolyl)ethylamine salt of (R)-3,3,3-trifluoro-2-hydroxy-2-methylpropionic acid with an optical purity of 95% ee. Melting point: 163 to 164° C.; Specific rotation $[\alpha]D^{25}$=+62°(c=0.55, methanol)

Example 2

In 0.79 g of acetone, 148 mg(0.93 mmol) of racemic 3,3,3-trifluoro-2-hydroxy-2-methylpropionic acid was dissolved at 20° C. To this solution was added, at that temperature, a solution prepared by dissolving in advance 135 mg(0.45 mmol) of (S)-N-benzyl-1-phenyl-2-(p-tolyl) ethylamine in 0.79 g of acetone, and then stirred to mix.

The solution after mixing was left standing at 20° C. for 18 hours to precipitate crystals.

The crystals formed were collected by filtration, washes with 0.79 g of acetone and then dried to yield 17 mg of (S)-N-benzyl-1-phenyl-20(p-tolyl)ethylamine salt of (R)-3,3,3-trifluoro-2-hydroxy-2-methylpropionic acid with an optical purity of 99% ee.

Example 3

In 0.78 g of acetonitrile, 147 mg(0.93 mmol) of racemic 3,3,3-trifluoro-2-hydroxy-2-methylpropionic acid was dissolved at 20° C. To this solution was added, at that temperature, a solution prepared by dissolving in advance 135 mg(0.45 mmol) of (S)-N-benzyl-1-phenyl-2-(p-tolyl) ethylamine in 0.78 g of acetonitrile, and then stirred to mix.

The solution after mixing was left standing at 20° C. for 18 hours to precipitate crystals.

The crystals formed were collected by filtration, washed with 1.56 g of acetonitrile and then dried to yield 50 mg of (SS)-N-benzyl-1-phenyl-2-(p-tolyl)ethylamine salt of (R)-3,3,3-trifluoro-2-hydroxy-2-methylpropionic acid with an optical purity of 96% ee.

Example 4

In 2.96 g of t-butyl methyl ether, 157 mg(1.00 mmol) of racemic 3,3,3-trifluoro-2-hydroxy-2-methylpropionic acid was dissolved at 55° C. To this solution was added, at that temperature, a solution prepared by dissolving in advance 152 mg(1.00 mmol) of (1R,2S)-(-)-norephedrine in 2.96 g of t-butyl methyl ether, and then stirred to mix.

After ascertaining the precipitation of crystals, the mixture was cooled gradually to 20° C. over 3 hours with stirring. The crystals formed were collected by filtration, washed with 1.48 g of t-butyl methyl ether and then dried to yield 77 mg of (1R,2S)-(-)-norephedrine salt of (S)-3,3,3-trifluoro-2-hydroxy-2-methylpropionic acid with an optical purity of 78% ee. Melting point: 149 to 150° C.; Specific rotation $[\alpha]D^{25}$=-33°(c=0.37, methanol)

Example 5

In a mixed solvent of 0.17 g of n-butanol and 0.87 g of toluene, 149 mg(0.94 mmol) of racemic 3,3,3-trifluoro-2-hydorxy-2-methylpropionic acid was dissolved at 50° C. To this solution was added, at that temperature, a solution prepared by dissolving in advance 148 mg(0.98 mmol) of (1R,2S)-(-)-norephedrine in a mixed solvent of 0.17 g of n-butanol and 0.87 g of toluene, and then stirred to mix.

After ascertaining the precipitation of crystals, the mixture was cooled gradually to 20° C. over 3 hours with stirring.

The crystals formed were collected by filtration, washed with a mixed solvent of 0.35 g of n-butanol and 1.73 g of toluene and then dried to yield 78 mg of (1R,2S)-(-)-norephedrine salt of (S)-3,3,3-trifluoro-2-hydroxy-2-methylpropionic acid with an optical purity of 84% ee.

Example 6

In 1.48 g of t-butyl methyl ether, 159 mg(1.01 mmol) of racemic 3,3,3-trifluoro-2-hydroxy-2-methylpropionic acid was dissolved at 45° C. To this solution was added, at that temperature, a solution prepared by dissolving in advance 172 mg(0.54 mmol) of (S)-N-(3-benzyloxybenzyl)-α-methylbenzylamine in 1.48 g of t-butyl methyl ether, and then stirred to mix. After ascertaining the precipitation of crystals, the mixture was cooled gradually to 35° C. over 0.5 hour with stirring.

The crystals formed were collected by filtration, washed with 2.96 g of t-butyl methyl ether and then dried to yield 61 mg of (S)-N-(3-benzyloxybenzyl-α-methylbenzylamine salt of (R)-3,3,3-trifluoro-2-hydroxy-2-methylpropionic acid with an optical purity of 95% ee. Melting point: 131 to 132° C.; Specific rotation $[\alpha]D^{25}$=5.8°(c=0.59, methanol)

Example 7

In 4.77 g of 2-propanol, 4.77 g (15.8 mmol) of (S)-N-benzyl-1-phenyl-2-(p-tolyl) ethylamine was dissolved at 50° C. To this solution was added, at that temperature, a solution prepared by dissolving in advance 5.04 g (31.9 mmol) of racemic 3,3,3-trifluoro-2hydroxy-2methylpropionic acid in 10.1 g of t-butyl methyl ether, and then stirred to mix.

After ascertaining the precipitation of crystals, the mixture was cooled gradually to 0° C. over 3 hours with stirring, and thereafter held at that temperature for 2 hours.

The crystals formed were collected by filtration, washed with 35 g of 0° C. t-butyl methyl ether and then dried to yield 5.57 g of (S)-N-benzyl-1-phenyl-2-(p-tolyl)ethylamine salt of (R)-3,3,3-trifluoro-2-hydroxy-2-methylpropionic acid with an optical purity of 91% ee.

Example 8

In 29.1 g of toluene, 4.77 g(15.8 mmol) of (S)-N-benzyl-1-phenyl-2-(p-tolyl) ethylamine was dissolved at 60 ° C. To this solution was added, at that temperature, a solution prepared by dissolving in advance 5.04 g (31.9 mmol) of racemic 3,3,3-trifluoro-2-hydroxy-2-methylpropioniic acid in 10.1 g of t-butyl methyl ether, and then stirred to mix.

After cooling to room temperature, a seed crystal was inoculated. After ascertaining the precipitation of crystals, the mixture was stirred overnight at room temperature, and subsequently cooled gradually to 0° C. over 2 hours with stirring.

The crystals formed were collected by filtration, washed with 13 g of 0° C. toluene and then dried to yield 4.12 g of (S)-N-benzyl-1-phenyl-2-(p-tolyl)ethylamine salt of (R)-3,3,3-trifluoro-2hydroxy-2-methylpropionic acid with an optical purity of 94% ee.

Example 9

In 5.0 g of toluene, 0.48 g (1.04 mmol) of the (S)-N-benzyl-1-phenyl- 2-(p-tolyl)ethylamine salt of (R)-3,3,3-trifluoro-2-hydroxy-2-methylpropionic acid with an optical purity of 91% ee which was obtained in Example 7 was dissolved at 60° C., and then cooled gradually to 20° C. with stirring.

The crystals formed were collected by filtration, washed with 2.0 g of toluene and then dried to yield 0.42 g of (S)-N-benzyl-1-phenyl-2-(p-tolyl)ethylamine salt of (R)-3,3,3-trifluoro-2-hydroxy-2-methylpropionic acid with an optical purity of 99% ee.

Example 10

In ethanol, 4.90 g (10.7 mmol) of the (S)-N-benzyl-1-phenyl-2-(p-tolyl)ethylamine salt of (R)-3,3,3-trifluoro-2-hydroxy-2-methylpropionic acid with an optical purity of 91% ee which was obtained in Example 7 was dissolved at 60° C., and then cooled gradually to 0° C. with stirring.

The crystals formed were collected by filtration, washed with ethanol and then dried to yield 3.80 g of (S)-N-benzyl-1-phenyl-2-(p-tolyl)ethylamine salt of (R)-3,3,3-trifluoro-2-hydroxy-2-methylpropionic acid with an optical purity of 98% ee.

Example 11

In 10.3 g of methanol, 3.50 g (7.62 mmol) of the (S)-N-benzyl-1-phenyl-2-(p-tolyl)ethylamine salt of (R)-3,3,3-trifluoro-2-hydroxy-2-methylpropionic acid with an optical purity of 94% ee which was obtained in Example 8 was dissolved at 60° C., inoculated at 5° C., and then cooled gradually to 0° C. over 5 hours with stirring.

The crystals formed were collected by filtration, washed with 7.4 g of 0° C. methanol and then dried to yield 2.81 g of (S)-N-benzyl-1-phenyl-2-(p-tolyl)ethylamine salt of (R)-3,3,3-trifluoro-2-hydroxy-2-methylpropionic acid with an optical purity of >99% ee.

Example 12

To 22 mg (0.05 mmol) of the salt obtained in Example 1, 2 ml of a 2N aqueous sodium hydroxide solution and 5 ml of t-butyl methyl ether were added and the salt was completely dissolved. The aqueous layer was then isolated.

Subsequently, to the isolated aqueous layer, 5 ml of a 2N hydrochloric acid solution and 5 ml of t-butyl methyl ether were added and stirred, followed by isolating the t-butyl methyl ether layer. The isolated t-butyl methyl ether solution was concentrated under reduced pressure to remove the solvent so as to precipitate a solid. The precipitated solid was washed with 0.5 ml of n-hexane, isolated by filtration and then dried to yield 7 mg of (R)-3,3,3-trifluoro-2-hydroxy-2-methylpropionic acid with an optical purity of 95% ee.

Example 13

A solution of 151 mg (0.96 mmol) of racemic 3,3,3-trifluoro-2-hydroxy-2-methylpropionic acid in 0.74 g of t-butyl methyl ether was added at 25° C. to a solution of 189 mg (0.53 mmol) of (R)-N-(4-phenylbenzyl)-2,4-dichlorobenzylamine in 0.74 g of t-butyl methyl ether, and the resulting solution was mixed under stirring. Dry nitrogen gas was blown onto the surface of the solution to concentrate the solution so as to precipitate crystals. The precipitated crystals were washed with 0.74 g of t-butyl methyl ether and the crystals were collected by filtration and the collected crystals were washed with 0.74 g of t-butyl methyl ether and dried to yield 166 mg of (R)-N-(4-phenylbenzyl)-2,4-dichloro-α-methylbenzylamine salt of (S)-3,3,3-trifluoro-2-hydroxy-2-methylpropionic acid with an optical purity of 86% ee.

Example 14

A solution of 166 mg (1.05 mmol) of racemic 3,3,3-trifluoro-2-hydroxy-2-methylpropionic acid in 0.74 g of t-butyl methyl ether was added at 25° C. to a solution of 205 mg (0.54 mmol) of (S)-N-(4-phenylbenzyl)-1-phenyl-2-(p-tolyl)ethylamine in 0.74 g of t-butyl methyl ether, and the resulting solution was mixed under stirring. The solution was left standing at the same temperature for 1 day to precipitate crystals. The precipitated crystals were washed with 0.74 g of t-butyl methyl ether and the crystals were collected by filtration and the collected crystals were washed with 0.74 g of t-butyl methyl ether and dried to yield 203 mg of (S)-N-(4-phenylbenzyl)-1-phenyl-2-(p-tolyl)ethylamine salt of (R)-3,3,3-trifluoro-2-hydroxy-2-methylpropionic acid with an optical purity of 72% ee.

Melting point: 168 to 170° C.; Specific rotation $[\alpha]_D^{25}$=+46° (c=0.80, methanol)

Example 15

A solution of 154 mg (0.97 mmol) of racemic 3,3,3-trifluoro-2-hydroxy-2-methylpropionic acid in 0.74 g of t-butyl methyl ether was added at 25° C. to a solution of 195 mg (0.50 mmol) of (R)-N-(3-benzyloxybenzyl)-2,4-dichloro-α-methylbenzylamine in 0.74 g of t-butyl methyl ether, and the resulting solution was mixed under stirring. The solution was left standing at 5° C. for 1 day to precipitate crystals. The precipitated crystals were washed with 0.74 g of t-butyl methyl ether and dried to yield 216 mg of (R)-N-(3-benzyloxybenzyl)-2,4-dichloro-α-methylbenzylamine salt of (S)-3,3,3-trifluoro-2-hydroxy-2-methylpropionic acid with an optical purity of 61% ee.

Example 16

A solution of 164 mg (1.04 mmol) of racemic 3,3,3-trifluoro-2-hydroxy-2-methylpropionic acid dissolved in 0.78 g of acetonitrile at 55° C. was added at the same temperature to a solution of 157 mg (0.56 mmol) of (R)-N-benzyl-2,4-dichloro-α-methylbenzylamine dissolved in 0.78 g of acetonitrile at 55° C., and the resulting solution was mixed under stirring. The solution was inoculated at 40° C. and cooled to 25° C. under stirring over 3 hours. The precipitated crystals were washed with 0.78 g of acetonitrile and dried to yield 65 mg of (R)-N-benzyl-2,4-dichloro-α-methylbenzylamine salt of (S)-3,3,3-trifluoro-2-hydroxy-2-methylpropionic acid with an optical purity of 98% ee.

Example 17

A solution of 163 mg (1.03 mmol) of racemic 3,3,3-trifluoro-3-hydroxy-2-methylpropionic acid dissolved in 0.89 g of ethyl acetate at 55° C. was added at the same temperature to a solution of 160 mg (0.57 mmol) of (R)-N-benzyl-2,4-dichloro-α-methylbenzylamine dissolved in 0.89 g of ethyl acetate at 55° C., and the resulting solution was mixed under stirring. The solution was inoculated at 10° C. After confirming precipitation, stirring was continued for 16 hours at 10° C. The precipitated crystals were collected by filtration and washed with 0.89 g of ethyl acetate to yield 42 mg of (R)-N-benzyl-2,4-dichloro-α-methylbenzylamine salt of (S)-3,3,3-trifluoro-2-hydroxy-2-methylpropionic acid with an optical purity of >99% ee.

Example 18

A solution of 159 mg (1.00 mmol) of racemic 3,3,3-trifluoro-2-hydroxy-2-methylpropionic acid dissolved in a mixed solvent of 0.50 g of water and 0.40 g of 2-propanol at 55° C. was added at the same temperature to a solution of 159 mg (0.57 mmol) of (R)-N-benzyl-2,4-dichloro-α-methylbenzylamine dissolved in a mixed solvent of 0.50 g of water and 0.40 g of 2-propanol at 55° C., and the resulting solution was mixed under stirring. The solution was inoculated at 40° C. and cooled to 25° C. under stirring over 3 hours. The precipitated crystals were collected by filtration and washed with a mixed solution of 0.50 g of water and 0.40 g of 2-propanol and dried to yield 109 mg of (R)-N-benzyl-2,4-dichloro-α-methylbenzylamine salt of (S)-3,3,3-trifluoro-2-hydroxy-2-methylpropionic acid with an optical purity of 97% ee.

Melting point: 152 to 154° C.; Specific rotation $[\alpha]_D^{25}$=−24° (c=0.62, methanol)

Example 19

A solution of 164 mg (1.04 mmol) of racemic 3,3,3-trifluoro-2-hydroxy-2-methylpropionic acid dissolved in 2.22 g of t-butyl methyl ether at 55° C. was added at 55° C. to a solution of 180 mg (0.51 mmol) of (R)-N-(4-phenylbenzyl)-2,4-dichloro-α-methylbenzylamine in 2.22 g of t-butyl methyl ether, and the resulting solution was mixed under stirring. The solution was inoculated at 55° C. and then cooled to 25° C. under stirring over 1 hour. The precipitated crystals were collected by filtration and the collected crystals were washed with 0.74 g of t-butyl methyl ether and dried to yield 144 mg of (R)-N-(4-phenylbenzyl)-2,4-dichloro-α-methylbenzylamine salt of (S)-3,3,3-trifluoro-2-hydroxy-2-methylpropionic acid with an optical purity of 97% ee.

Example 20

A solution of 163 mg (1.03 mmol) of racemic 3,3,3-trifluoro-2-hydroxy-2-methylpropionic acid dissolved in 0.78 g of acetonitorile at 55° C. was added at 55° C. to a solution of 184 mg (0.52 mmol) of (R)-N-(4-phenylbenzyl)-2,4-dichloro-α-methylbenzylamine in 0.78 g of acetonitorile and the resulting solution was mixed under stirring. The solution was inoculated at 55° C. and then cooled to 25° C. under stirring over 1 hour. The precipitated crystals were collected by filtration and the collected crystals were washed with 0.78 g of acetonitorile and dried to yield 149 mg of (R)-N-(4-phenylbenzyl)-2,4-dichloro-α-methylbenzylamine salt of (S)-3,3,3-trifluoro-2-hydroxy-2-methylpropionic acid with an optical purity of 97% ee.

Example 21

A solution of 161 mg (1.02 mmol) of racemic 3,3,3-trifluoro-2-hydroxy-2-methylpropionic acid dissolved in 0.86 g of toluene at 55° C. was added at 55° C. to a solution of 189 mg (0.53 mmol) of (R)-N-(4-phenylbenzyl)-2,4-dichloro-α-methylbenzylamine in 0.86 g of toluene and the resulting solution was mixed under stirring. The solution was inoculated at 40° C. and then cooled to 25° C. under stirring over 0.5 hour. The precipitated crystals were collected by filtration and the collected crystals were washed with 0.86 g of toluene and dried to yield 59 mg of (R)-N-(4-phenylbenzyl)-2,4-dichloro-α-methylbenzylamine salt of (S)-3,3,3-trifluoro-2-hydroxy-2-methylpropionic acid with an optical purity of 99% ee.

Example 22

A solution of 165 mg (1.04 mmol) of racemic 3,3,3-trifluoro-2-hydroxy-2-methylpropionic acid dissolved in 0.78 g of acetone at 55° C. was added at 55° C. to a solution of 177 mg (0.49 mmol) of (R)-N-(4-phenylbenzyl)-2,4-dichloro-α-methylbenzylamine in 0.78 g of acetone and the resulting solution was mixed under stirring. The solution was inoculated at 40° C. and then cooled to 25° C. under stirring over 0.5 hour. The precipitated crystals were collected by filtration and the collected crystals were washed with 0.78 g of acetone and dried to yield 88 mg of (R)-N-(4-phenylbenzyl)-2,4-dichloro-α-methylbenzylamine salt of (S)-3,3,3-trifluoro-2-hydroxy-2-methylpropionic acid with an optical purity of 99% ee or more.

Example 23

A solution of 166 mg (1.05 mmol) of racemic 3,3,3-trifluoro-2-hydroxy-2-methylpropionic acid dissolved in 0.89 g of ethyl acetate at 55° C. was added at 55° C. to a solution of 190 mg (0.53 mmol) of (R)-N-(4-phenylbenzyl)-2,4-dichloro-α-methylbenzylamine in 0.89 g of ethyl acetate and the resulting solution was mixed under stirring, The solution was inoculated at 55° C. and then cooled to 25° C. under stirring over 1 hour. The precipitated crystals were collected by filtration and the collected crystals were washed with 0.89 g of ethyl acetate and dried to yield 116 mg of (R)-N-(4-phenylbenzyl)-2,4-dichloro-α-methylbenzylamine salt of (S)-3,3,3-trifluoro-2-hydroxy-2-methylpropionic acid with an optical purity of 99% ee.

Example 24

A solution of 172 mg (1.09 mmol) of racemic 3,3,3-trifluoro-2-hydroxy-2-methylpropionic acid dissolved in 2.22 g of t-butyl methyl ether at 55° C. was added at 55° C. to a solution of 192 mg (0.50 mmol) of (R)-N-(3-benzyloxybenzyl)-2,4-dichloro-α-methylbenzylamine in 2.22 g of t-butyl methyl ether and the resulting solution was mixed under stirring. The solution was inoculated at 55° C. and then cooled to 25° C. under stirring over 1 hour. The precipitated crystals were collected by filtration and the collected crystals were washed with 0.74 g of t-butyl methyl ether and dried to yield 201 mg of (R)-N-(3-benzyloxybenzyl)-2,4-dichloro-α-methylbenzylamine salt of (S)-3,3,3-trifluoro-2-hydroxy-2-methylpropionic acid with an optical purity of 97% ee.

Example 25

A solution of 165 mg (1.05 mmol) of racemic 3,3,3-trifluoro-2-hydroxy-2-methylpropionic acid dissolved in 0.78 g of acetonitorile at 55° C. was added at 55° C. to a solution of 194 mg (0.50 mmol) of (R)-N-(3-benzyloxybenzyl)-2,4-dichloro-α-methylbenzylamine in 0.78 g of in acetonitrile and the resulting solution was mixed under stirring. The solution was inoculated at 25° C. to precipitate. Then, the precipitated crystals were collected by filtration and the collected crystals were washed with 0.78 g of acetonitorile and dried to yield 77 mg of (R)-N-(3-benzyloxybenzyl)-2,4-dichloro-α-methylbenzylamine salt of (S)-3,3,3-trifluoro-2-hydroxy-2-methylpropionic acid with an optical purity of 99% ee.

Example 26

A solution of 2.46 g (15.56 mmol) of racemic 3,3,3-trifluoro-2-hydroxy-2-methylpropionic acid dissolved in a mixed solvent of 20.82 g of water and 16.65 g of 2-propanol at 55° C. was added at 55° C. to a solution of 2.80 g (7.85 mmol) of (R)-N-(4-phenylbenzyl)-2,4-dichloro-α-methylbenzylamine in a mixed solvent of 20.78 g of water and 16.62 g of 2-propanol and the resulting solution was mixed under stirring. The solution was inoculated at 55° C. and then cooled to 25° C. under stirring over 1.5 hours and kept at the temperature for 2 hours. The precipitated crystals were collected by filtration and the collected crystals were washed with a mixed solvent of 2.50 g of water and 2.00 g of 2-propanol and dried to yield 2.75 g of (R)-N-(4-phenylbenzyl)-2,4-dichloro-α-methylbenzylamine salt of (S)-3,3,3-trifluoro-2-hydroxy-2-methylpropionic acid with an optical purity of 97% ee.

Melting point: 168 to 170° C.; Specific rotation [α]D25=−18° (c=0.88, methanol)

Example 27

A solution of 2.50 g (15.79 mmol) of racemic 3,3,3-trifluoro-2-hydroxy-2-methylpropionic acid dissolved in a mixed solvent of 9.63 g of water and 7.72 g of 2-propanol at 55° C. was added at 55° C. to a solution of 2.12 g (5.48 mmol) of (R)-N-(3-benzyloxybenzyl)-2,4-dichloro-α-methylbenzylamine in a mixed solvent of 9.74 g of water and 7.78 g of 2-propanol and the resulting solution was mixed under stirring. The solution was inoculated at 55° C. and then cooled to 25° C. under stirring over 1.5 hours and kept at the temperature for 1 day. The precipitated crystals were collected by filtration and the collected crystals were washed with a mixed solvent of 2.50 g of water and 2.00 g of 2-propanol and dried to yield 2.38 g of (R)-N-(3-benzyloxybenzyl)-2,4-dichloro-α-methylbenzylamine salt of (S)-3,3,3-trifluoro-2-hydroxy-2-methylpropionic acid with an optical purity of 98% ee.

Melting point: 142 to 144° C.; Specific rotation [α]D25=−16° (c=0.80, methanol)

Example 28

In 600 ml of ethanol, 27.19 g (0.224 mmol) of (S)-α-methylbenzylamine and 50.00 g (0.236 mmol) of 3-benzyloxybenzaldehyde were stirred at room temperature for 8 hours. After ascertaining the disappearance of the amine, 8.15 g (0.215 mol) of sodium borohydride was added at room temperature and stirred at 30° C. to 35° C. for 8 hours.

After the reaction, 185.00 g of 10% hydrochloric acid was added at room temperature. The resulting mixture was then concentrated under reduced pressure. The residue was dissolved in 700 ml of water and washes with 500 ml of diethyl ether.

The resulting aqueous layer was adjusted to pH>10 with a 20% aqueous sodium hydroxide solution and extracted with 500 ml of toluene, which was then washed with 250 ml of water and concentrated under reduced pressure to yield 54.71 g (0.172 mmol) of (S)-N-(3-benzyloxybenzyl)-α-methylbenzylamine (Yield: 77.4%; Purity: 99.5%)

NMR spectrum data (δ ppm, CDCl$_3$) 1.34 (d) 2H; 1.54 (s) 1H; 3.61 (q) 2H; 3.79 (q) 1H; 5.06 (s) 2H; 6.83–7.46 (m) 14H.

Example 29

Following the procedure of Example 28 except for using 4-benzyloxybenzaldehyde in place of 3-benzyloxybenzaldehyde, operations were conducted.

(S)-N-(4-benzyloxybenzyl)-α-methylbenzylamine was obtained in an amount of 57.3 g (0.181 mmol). (Yield: 80.4%; Purity: 99.3%)

NMR spectrum data (δ ppm, CDCl$_3$) 1.34 (d) 2H; 1.48 (s) 1H; 3.55 (q) 2H; 3.78 (q) 1H; 5.05 (s) 2H; 6.90–7.45 (m) 14H.

Example 30

7.48 g (0.0394 mmol) of (R)-2,4-dichloro-α-methylbenzylamine and 10.03 g (0.0473 mol) of 3-benzyloxybenzaldehyde were mixed in a mixed solvent of 50 ml of t-butyl methyl ether and 10 ml of methanol under stirring at room temperature for 8 hours. After ascertaining the disappearance of the amine, 20 ml of methanol was added thereto and 2.63 g (0.0695 mmol) of sodium borohydride was added at room temperature and stirred at that temperature for 13 hours.

After the reaction, 13 ml of 36% hydrochloric acid and 10 ml of water were added at room temperature. The resulting mixture was then concentrated under reduced pressure. The liquid residue was dissolved in 25 ml of t-butyl methyl ether under stirring and then left standing to precipitate, which was removed by filtration. To the obtained filtrate was made alkaline by adding a solution of 21.35 g of sodium hydroxide dissolved in 200 ml of water and the resulting solution was subjected to extraction with 500 ml of t-butyl methyl ether. The extract was evaporated to yield 14.51 g (0.0376 mol) of crude (R)-N-(3-benzyloxybenzyl)-2,4-dichloro-α-methylbenzylamine. (Yield:95.5%, Purity 80.8%)

To 14.51 g (0.0376 mol) of crude (R)-N-(3-benzyloxybenzyl)-2,4-dichloro-α-methylbenzylamine obtained were added 4 ml of 36% hydrochloric acid and 30 ml of t-butyl methyl ether, the resulting solution was left standing at room temperature for 2 days to precipitate. The precipitated crystals were separated by filtration and washed with 25 ml of t-butyl methyl ether. Then the crystals were contacted with an alkaline solution of 1.84 g of sodium hydroxide in 50 ml of water, and extracted with 300 ml of t-butyl methyl ether under alkaline condition. The extract was evaporated under reduced pressure to yield 5.62 g (0.045 mol) of purified (R)-N-(3-benzyloxybenzyl)-2,4-dichloro-α-methylbenzylamine. (Yield: 37.0%, Purity 99.8%)

NMR spectrum data (δ ppm, CDCl$_3$) 1.30 (d) 3H; 1.57 (s) 1H; 3.57 (d) 2H; 4.27 (q) 1H; 5.05 (s) 2H; 7.20–7.58 (m) 12H.

Example 31

7.34 g (0.0386 mol) of (R)-2,4-dichloro-α-methylbenzylamine and 9.73 g (0.0458 mol) of 4-benzyloxybenzaldehyde were mixed in a mixed solvent of 50 ml of t-butyl methyl ether and 20 ml of methanol and stirred at room temperature for 9 hours. After ascertaining the disappearance of the amine, 1.75 g (0.0463 mol) of sodium borohydride was added thereto at room temperature and stirred at that temperature for 5 hours.

After the reaction, 13 ml of 36% hydrochloric acid and 30 ml of water were added at room temperature. Precipitated crystals were collected by filtration and washed with 25 ml of t-butyl methyl ether. Then the crystals were mixed with alkaline solution containing 2.93 g of sodium hydroxide in 100 ml of water and extracted with 900 ml of t-butyl methyl ester under alkaline condition. The extract was evaporated under reduced pressure to yield 12.53 g (0.0324 mol) of purified (R)-N-(4-benzyloxybenzyl)-2,4-dichloro-α-methylbenzylamine. (Yield: 84.0%, Purity 99.4%)

NMR spectrum data (δ ppm, CDCl$_3$) 1.30 (d) 3H; 1.63 (s) 1H; 3.52 (s) 2H; 4.27 (q) 1H; 5.04 (s) 2H; 6.88–7.58 (m) 12H.

Example 32

7.24 g (0.0381 mol) of (R)-2,4-dichloro-α-methylbenzylamine and 9.06 g (0.0457 mol) of 3-phenoxybenzaldehyde were mixed in 100 ml of ethanol and stirred at room temperature for 6 hours. After ascertaining the disappearance of the amine, 1.75 g (0.0463 mol) of sodium borohydride was added thereto at room temperature and stirred at that temperature for 3 hours.

After the reaction, 10 ml of 36% hydrochloric acid and 10 ml of water were added at room temperature and evaporated under reduced pressure. To the obtained residue were added 100 ml of t-butyl methyl ether and 100 ml of water and stirred. The solution was left standing to precipitate. Precipitated crystals were washed with 100 ml of t-butyl methyl ether and then mixed with alkaline solution containing 6.98 g of sodium hydroxide in 100 ml of water and made alkaline and extracted with 150 ml of chloroform under alkaline condition. The extract was evaporated under reduced pressure to yield 13.5 g (0.0361 mol) of purified (R)-N-(3-phenoxybenzyl)-2,4-dichloro-α-methylbenzylamine. (Yield: 94.8%, Purity 94.1%)

NMR spectrum data (δ ppm, CDCl$_3$) 1.29 (d) 3H; 1.58 (s) 1H; 3.57 (d) 2H; 4.25 (q) 1H; 6.95–7.56 (m) 12H.

Example 33

7.06 g (37.1 mol) of (R)-2,4-dichloro-α-methylbenzylamine and 8.13 g (44.6 mmol) of 4-phenylbenzaldehyde were mixed in 50 ml of t-butyl methyl ether and stirred at room temperature for 1 hour. After ascertaining the disappearance of the amine, 30 ml of methanol was added thereto and 2.60 g (68.7 mmol) of sodium borohydride was gradually added at room temperature and stirred at room temperature for 16 hours.

After the reaction, 13 ml of 36% hydrochloric acid and 10 ml of water were added at room temperature and evaporated under reduced pressure to yield crystals. To the obtained crystals was added 25 ml of t-butyl methyl ether, stirred and separated the crystals by filtration. The crystals were washed with 50 ml of t-butyl methyl and then mixed with alkaline solution containing 2.87 g of sodium hydroxide in 100 ml of water and extracted with 800 ml of t-butyl methyl ether under alkaline condition. The extract was evaporated under reduced pressure to yield 9.65 g (27.1 mmol) of (R)-N-(4-phenylbenzyl)-2,4-dichloro-α-methylbenzylamine. (Yield: 72.9%, Purity 99.1%)

NMR spectrum data (δ ppm, CDCl$_3$) 1.34 (d) 3H; 1.60 (s) 1H; 3.64 (s) 2H; 4.32 (q) 1H; 7.25–7.62 (m) 12H.

Example 34

0.12 g (0.97 mmol) of (S)-α-methylbenzylamine and 0.25 g (1.19 mmol) of 3-benzyloxybenzaldehyde are mixed in 4 ml of t-butyl methyl ether and stirred for three days at room temperature, and then evaporated under reduced pressure to give 0.35 g (1.12 mmol) of (S)-N-(3-benzyloxybenzylidene)-α-methylbenzylamine (Yield: 115%, purity 85%).

NMR spectrum data (δ ppm, CDCl$_3$) 1.58 (d) 3H; 4.54 (q) 1H; 5.10 (s) 2H; 7.04–7.50 (m) 14H; 8.33 (s) 1H.

Example 35

0.11 g (0.93 mmol) of (S)-α-methylbenzylamine and 0.26 g (1.23 mmol) of 4-benzyloxybenzaldehyde are mixed in 4 ml of t-butyl methyl ether and stirred for three days at room temperature, and then evaporated under reduced pressure to give a residue, which was then washed with 5 ml of n-hexane, filtered, and dried to give 0.24 (0.77 mmol) of (S)-N-(4-benzyloxybenzylidene)-α-methylbenzylamine (Yield: 83%, purity 90%).

NMR spectrum data (δ ppm, CDCl$_3$) 1.57 (d) 3H; 4.50 (q) 1H; 5.08 (s) 2H; 6.97–7.84 (m) 14H; 8.29 (s) 1H.

Example 36

In Example 34 (R)-2,4-dichloro-α-methylbenzylamine was used in place of (S)-α-methylbenzylamine and similar operations were conducted to obtain 0.43 g (1.11 mmol) of (R)-N-(3-benzyloxybenzylidene)-2,4-dichloro-α-methylbenzylamine (Yield: 109%, Purity: 90%)

NMR spectrum data (δ ppm, CDCl$_3$) 1.51 (d) 3H; 4.92 (q) 1H; 5.10 (s) 2H; 7.02–7.74 (m) 12H; 8.35 (s) 1H.

Example 37

In Example 36 4-benzyloxybenzaldehyde was used in place of 3-benzyloxybenzaldehyde and similar operations were conducted to obtain 0.47 g (1.23 mmol) of (R)-N-(4-benzyloxybenzylidene)-2,4-dichloro-α-methylbenzylamine (Yield: 100%, Purity: 98%)

NMR spectrum data (δ ppm, CDCl₃) 1.49 (d) 3H; 4.88 (q) 1H; 5.09 (s) 2H; 6.98–7.74 (m) 12H; 8.31 (s) 1H.

Example 38

In Example 36 4-phenylbenzaldehyde was used in place of 3-benzyloxybenzaldehyde and similar operations were conducted to obtain 0.391 g (1.10 mmol) of (R)-N-(4-phenylbenzylidene)-2,4-dichloro-α-methylbenzylamine (Yield: 113%, Purity: 89%)

NMR spectrum data (δ ppm, CDCl₃) 1.53 (d) 3H; 4.95 (q) 1H; 7.23–7.86 (m) 12H; 8.42 (s) 1H.

Example 39

In Example 36 3-phenoxylbenzaldehyde was used in place of 3-benzyloxybenzaldehyde and similar operations were conducted to obtain 0.420 g (1.13 mmol) of (R)-N-(3-phenoxylbenzylidene)-2,4-dichloro-α-methylbenzylamine (Yield: 116%, Purity: 86%)

NMR spectrum data (δ ppm, CDCl₃) 1.50 (d) 3H; 4.92 (q) 1H; 7.00–7.71 (m) 12H; 8.34 (s) 1H.

Comparative Example 1

In 2.37 g of methanol, 153 mg (0.96 mmol) of racemic 3,3,3-trifluoro-2-hydroxy-2-methylpropionic acid was dissolved at 45° C. To this solution was added, at that temperature, a solution prepared by dissolving in advance 200 mg (0.51 mmol) of (−)-brucine in 2.37 g of methanol, and then stirred to mix.

The solution after mixing was left standing at room temperature for 2 days to precipitate crystals.

The crystals formed were collected by filtration, washed with 3.17 g of methanol and then dried to yield 115 mg of (−)-brucine salt of (S)-3,3,3-trifluoro-2-hydroxy-2-methylpropionic acid with an optical purity of 42% ee.

Comparative Example 2

In 1.48 g of t-butyl methyl ether, 310 mg (1.96 mmol) of racemic 3,3,3-trifluoro-2-hydroxy-2-methylpropionic acid was dissolved at room temperature. To this solution was added, at that temperature, a solution prepared by dissolving in advance 235 mg (1.94 mmol) of (S)-α-methylbenzylamine in 1.48 g of t-butyl methyl ether, and then stirred to mix.

The solution was left standing thereafter for 3 days at 5° C., and resulted in no precipitation of crystals, the solvent was removed by blowing nitrogen onto the surface of the solution at room temperature to concentrate the solution so as to precipitate crystals.

The crystals formed were collected by filtration, washed with 1.48 g of t-butyl methyl ether and then dried to yield 253 mg of (S)-α-methylbenzylamine salt of (S)-3,3,3-trifluoro-2-hydroxy-2-methylpropionic acid with an optical purity of 5% ee.

What is claimed is:

1. An optically active amine compound of formula (4):

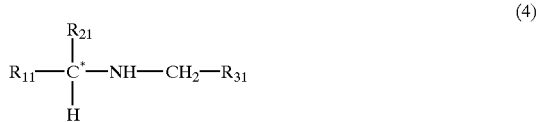

(4)

wherein an asymmetric carbon atom denoted by the symbol * is in S configuration or R configuration, $R_{11}$ represents (i) a phenyl group which may be substituted with at least one group selected from a C1–C4 alkyl group, a nitro group and a halogen atom, or (ii) a naphthyl group substituted with at least one group selected from a C1–C4 alkyl, a C1–C4 alkoxy group, a nitro group and a halogen atom, $R_{21}$ represents a C1–C4 alkyl group, or an aralkyl group which may be substituted, and $R_{31}$ is a 3-benzyloxyphenyl group or a 4-benzyloxyphenyl group, or a salt thereof.

2. The optically active amine compound of formula (4) according to claim 1, wherein $R_{11}$ represents (i) a phenyl group which may be substituted with at least one group selected from a C1–C4 alkyl group, a nitro group and a halogen atom, or (ii) a naphthyl group substituted with at least one group selected from a C1–C4 alkyl, a C1–C4 alkoxy group, a nitro group and a halogen atom, $R_{21}$ represents a C1–C4 alkyl group, or a C7–C12 aralkyl group, of which aryl group may be substituted with at least one group selected from a C1–C4 alkyl group, a C1–C4 alkoxy group, a nitro group, a halogen atom, a C6–C10 aryl group, a C6–C10 aryloxy group, a C7–C12 aralkyl group and a C7–C12 aralkyloxy group, the last four of which may be substituted on each aromatic ring with at least one group selected from a C1–C4 alkyl group, a C1–C4 alkoxy group and a halogen atom, and of which alkyl group may be substituted with a hydroxy group.

3. The optically active amine compound, or a salt thereof according to claim 2, wherein $R_{11}$ is a phenyl group and $R_{21}$ is a methyl group.

4. The optically active amine compound, or a salt thereof according to claim 2, wherein $R_{11}$ is a 2,4-dichlolorophenyl group and $R_{21}$ is a methyl group.

5. An optically active amine compound of formula (8);

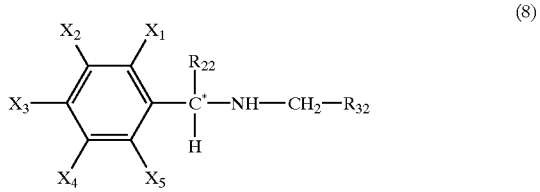

(8)

wherein $X_1$ represents a halogen atom or a lower alkyl group, $X_2$ to $X_5$ are the same or different and independently represent a hydrogen atom, a halogen atom, a nitro group or a lower alkyl group, $R_{22}$ represents a lower alkyl group, and $R_{32}$ represents an aryl group substituted with at least one group selected from a lower alkyl group, an aryl group and an aryloxy group, or a salt thereof.

6. The optically active amine compound of formula (8) according to claim 5, wherein the lower alkyl group in $X_1$ to $X_5$ and $R_{22}$ means a C1–C4 alkyl group, and $R_{32}$ represents a phenyl or naphthyl group substituted with a C1–C4 alkyl group, a phenyl group, a naphthyl group, a phenoxy group and a naphthoxy group.

7. The optically active amine compound of formula (8) according to claim 5, wherein $X_1$ and $X_3$ respectively represent a halogen atom and $X_2$, $X_4$ and $X_5$ are hydrogen atoms.

8. The optically active amine compound of formula (8) according to claim 7, wherein said halogen atom is a chlorine atom.

9. The optically active amine compound of formula (8) according to claim 6, 7 or 8, wherein $R_{32}$ is a 3-phenoxyphenyl group or a 4-phenylphenyl group.

10. The optically active amine compound according to claim 1, wherein $R_{11}$ represents (i) a phenyl group which may be substituted with at least one group selected from a C1–C4 alkyl group and a halogen atom, or (ii) a naphthyl group substituted with at least one group selected from a C1–C4 alkyl group and a halogen atom.

* * * * *